(12) United States Patent
Ueno et al.

(10) Patent No.: US 10,751,553 B2
(45) Date of Patent: Aug. 25, 2020

(54) RADIATION THERAPY APPARATUS

(71) Applicant: Hitachi, Ltd., Tokyo (JP)

(72) Inventors: Yuichiro Ueno, Tokyo (JP); Takahiro Tadokoro, Tokyo (JP); Yasushi Nagumo, Tokyo (JP); Katsunori Ueno, Tokyo (JP); Kouichi Okada, Tokyo (JP); Shuichi Hatakeyama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 7 days.

(21) Appl. No.: 16/304,701

(22) PCT Filed: Mar. 3, 2017

(86) PCT No.: PCT/JP2017/008433
§ 371 (c)(1),
(2) Date: Nov. 27, 2018

(87) PCT Pub. No.: WO2018/003179
PCT Pub. Date: Jan. 4, 2018

(65) Prior Publication Data
US 2019/0209870 A1 Jul. 11, 2019

(30) Foreign Application Priority Data

Jun. 28, 2016 (JP) .................. 2016-127309

(51) Int. Cl.
*A61N 5/10* (2006.01)
*A61B 6/00* (2006.01)

(52) U.S. Cl.
CPC ............ *A61N 5/1071* (2013.01); *A61B 6/425* (2013.01); *A61B 6/4216* (2013.01);
(Continued)

(58) Field of Classification Search
CPC .... A61B 6/4216; A61B 6/425; A61N 5/1042; A61N 5/1067; A61N 5/1071; A61N 5/1081; G01T 1/02
See application file for complete search history.

(56) References Cited

U.S. PATENT DOCUMENTS 5,538,494 A 7/1996 Matsuda
2003/0095625 A1 5/2003 Steinberg
(Continued)

FOREIGN PATENT DOCUMENTS

JP 07-303710 A 11/1995
JP 2001-056381 A 2/2001
(Continued)

OTHER PUBLICATIONS

Katsunori Uendo, et al., "Development of a optical fiber type dosimeter using near infrared luminescence", Japanese Journal of Medical Physics, Sep. 2015, vol. 35, Supplement No. 3.
(Continued)

*Primary Examiner* — Mark R Gaworecki
(74) *Attorney, Agent, or Firm* — Mattingly & Malur, PC

(57) ABSTRACT

A radiation therapy apparatus capable of improving the accuracy of a dose distribution includes an X-ray generation device that is provided at an arm portion of a rotation gantry, a radiation detector that is insertable into the body of a patient, a dose calculation device, and a feedback control device. An X-ray generated due to collision of an electron beam with a target in the X-ray generation device is applied to an affected part (cancer) of a patient on a bed. The radiation detector which is insertable into the body detects the X-ray applied to the affected part so as to output a photon to obtain a dose rate and a dose based thereon. The feedback control device either controls the X-ray generation device such that the obtained dose becomes a set dose or controls
(Continued)

the radiation generation device such that the obtained dose rate becomes a set dose rate.

12 Claims, 13 Drawing Sheets

(52) U.S. Cl.
CPC ......... *A61N 5/1042* (2013.01); *A61N 5/1067* (2013.01); *A61N 5/1081* (2013.01)

(56) References Cited

U.S. PATENT DOCUMENTS

| | | | |
|---|---|---|---|
| 2010/0152521 A1* | 6/2010 | Price | A61N 5/1027 600/7 |
| 2015/0238780 A1 | 8/2015 | Nishimura et al. | |

FOREIGN PATENT DOCUMENTS

| | | |
|---|---|---|
| JP | 2003-210596 A | 7/2003 |
| JP | 2007-139435 A | 6/2007 |
| JP | 2009-036752 A | 2/2009 |
| JP | 2013-538340 A | 10/2013 |
| JP | 2015-157003 A | 9/2015 |

OTHER PUBLICATIONS

Takahiro Tadokoro, et al., "Current Status and Vision of Study for Severe Accident Instrumentation Systems, Optical fiber-type radiationmonitor system", 2015 Annual Meeting of the Atomic Energy Society of Japan Proceedings, Lecture No. 117, issued on Mar. 5, 2015.
International Search Report of PCT/JP2017/008433 dated May 23, 2017.

* cited by examiner

RADIATION THERAPY APPARATUS

TECHNICAL FIELD

The present invention relates to a radiation therapy apparatus, and particularly to a radiation therapy apparatus suitable for being applied to an X-ray therapy apparatus, a particle beam therapy apparatus (for example, a particle beam therapy apparatus or a heavy particle beam therapy apparatus), and an electron beam therapy apparatus.

BACKGROUND ART

In Japan, the first cause of death is cancer, and cancer is steadily increasing. In recent Japan in which improvement in quality of life (QOL) is needed, therapy using radiation attracts attention as a cancer therapy method. In order to improve the QOL as the need, a radiation cancer therapy technique which is a seed becomes highly accurate, and radiation cancer therapy also starts to be widespread in Japan.

Radiation used for therapy includes an X-ray, a particle beam (a proton beam or a heavy particle beam), an electron beam, and a neutron beam. Particularly, in recent years, a particle beam therapy apparatus using a proton beam and a heavy particle beam therapy apparatus using a heavy particle beam (for example, a carbon beam) have been remarkably developed. A patient is irradiated with a particle beam by using the property that the proton beam and the heavy particle beam generate a dose peak (black peak) by being intensively applied with energy immediately after being stopped, and thus a dose can be applied to an affected part of cancer in a concentration manner, so that low invasive and highly accurate cancer therapy can be expected.

Also in cancer therapy using an X-ray, intensity-modulated radiotherapy (IMRT) and image-guided radiotherapy (IGRT) have been developed, and an effort to cause a dose in X-ray irradiation to concentrate on an affected part of cancer has been made. In accordance with sophistication of a radiation therapy apparatus, there is the need for improvement of the whole accuracy related to radiation therapy, such as the accuracy of a therapy plan and the accuracy of patient positioning, dose rate measurement for quality assurance (QA) of a therapy plan and a therapy apparatus.

In radiation therapy, an ionization chamber of which stability and reproducibility are favorable are widely used to measure a dose rate of radiation applied to a patient. However, the ionization chamber has a limit in miniaturization due to a detection principle thereof, and, instead thereof, a dose distribution measurement using a semiconductor detector which is relatively easily miniaturized is performed. In a case where even a signal processing system is included, the semiconductor detector also has a limit in miniaturization. Since a high voltage is required to be applied in such a radiation detector, it is difficult to insert the radiation detector into a patient's body, and to measure a dose rate. Such a detector generally has high density, has a greater interaction with radiation than a substance in the body and water, and thus the influence of the radiation detector cannot be disregarded.

As described above, in a situation in which an actual internal absorbed dose cannot be understood, a dose distribution of an affected part obtained through therapy planning has a margin by taking into consideration body motion of the patient due to respiration or the like. This is a cause of reducing the irradiation accuracy of radiation to an affected part. In the body of a patient, in a case where a normal part sensitive to radiation is present near an affected part which is a therapy target part, radiation therapy of the affected part is difficult.

In a radiation therapy apparatus disclosed in JP-A-2003-210596, radiation transmitted through a patient is detected by a radiation detector disposed outside the body of the patient irradiated with the radiation, and, in a case where there is body motion of the patient due to respiration or the like, there is a possibility that an accurate internal absorbed dose cannot be measured. Temporal changes of a position of an organ (affected part) in the body and a size of the organ in a radiation irradiation direction between the time of therapy planning and the time of therapy execution on the affected part using irradiation with radiation, and patient positioning during therapy also cause errors. An internal dose distribution of the patient is estimated through calculation using a dose which is obtained on the basis of a radiation detection signal output from the radiation detector outside the body. A calculation error in this estimation cannot be disregarded.

In order to reduce such errors, a radiation detector is preferably inserted into the body. A radiation detector inserted into the body is disclosed in JP-A-2001-56381. JP-A-2001-56381 discloses a technique in which a scintillation fiber and an optical transmission fiber are inserted into the body, and thus contribution of Cherenkov light which is noise can be removed such that a true radiation dose can be measured.

"Bragg Curve Measurement in Near-Infrared Single Photon Counting Mode", Katsunori UENO and others, the 110th Japanese Society of Health and Medical Sociology, Vol. 35, Supplement No. 3 (September, 2015), page 77 discloses an optical fiber type online dosimeter (internal dosimeter) which can measure an irradiation dose applied to a patient during proton therapy. The optical fiber type online dosimeter uses Nd:YAG for a detection unit, and performs single-photon counting on near-infrared light generated by Nd:YAG.

"Current status and vision of study for severe accident instrumentation system, 1. Optical fiber-type radiation monitor system", Takahiro TADOKORO and others, 2015 Annual Meeting of the Atomic Energy Society of Japan Proceedings, Lecture No. 117, issued on Mar. 5, 2015, discloses an optical fiber type radiation monitor, applied to a nuclear power plant, is configured with a detection unit, an optical fiber unit, and an optical measurement unit using Nd:YAG. The optical fiber type radiation monitor can measure a dose rate with the accuracy equal to or lower than ±4% FS in a range of a dose rate of $1.0 \times 10^{-2}$ to $9.54 \times 10^4$ Gy/h.

In radiation therapy using a radiation therapy apparatus, when radiation is applied, it is necessary that a dose in a normal tissue near an affected part which is an irradiation target is reduced as much as possible, and a large dose concentrates on the affected part. However, actually, a position of an affected part from a body surface is periodically changed due to respiration of a patient. Radiation respiration synchronized irradiation is performed in which a change of a position of an affected part due to respiration is detected, a cycle of the position change is measured, and the affected part is irradiated with radiation in synchronized with the cycle of the position change of the affected part. An example of the respiration synchronized irradiation is disclosed in JP-A-7-303710. In JP-A-7-303710, an ultrasonic tomographic apparatus generates a tomographic image of an affected part vicinity on the basis of an ultrasonic signal received by a probe provided on a body surface of a patient, and an image processing apparatus creates information indicating a cyclic position change of the affected part. The affected part is irradiated with a particle beam at a timing at which a position of the affected part is not changed in this cycle. JP-A-7-303710 also discloses that information indicating a cyclic position change of an affected part is created on the basis of an output signal from a respiration monitor instead of the ultrasonic tomographic apparatus.

JP-A-2015-157003 discloses a charged particle beam irradiation method in which an affected part of cancer is divided into a plurality of layers from a body surface in an irradiation direction of an ion beam, scanning with a thin ion beam is performed, and thus the ion beams are applied to a plurality of irradiation spots which are irradiation positions in each layer. Movement of an ion beam to a neighboring irradiation spot in each layer is performed by a scanning control device controlling a scanning electromagnet which changes a position of the ion beam.

In a depth direction of a human body, a dose distribution as illustrated in FIG. 6 of JP-A-2015-157003 is shown, a dose becomes the maximum at a Bragg peak, and the dose distribution is rapidly reduced at a depth exceeding the Bragg peak. Cancer therapy using an ion beam uses the property that a dose becomes the maximum at a Bragg peak, and the dose is rapidly reduced at a depth exceeding the Bragg peak.

CITATION LIST

Patent Literature

PTL 1: JP-A-2003-210596
PTL 2: JP-A-2001-56381
PTL 3: JP-A-7-303710
PTL 4: JP-A-2015-157003

Non-Patent Literature

NPL 1: "Bragg Curve Measurement in Near-Infrared Single Photon Counting Mode", Katsunori UENO and others, the 110th Japanese Society of Health and Medical Sociology, Vol. 35, Supplement No. 3 (September, 2015), page 77
NPL 2: "Current status and vision of study for severe accident instrumentation system, 1. Optical fiber-type radiation monitor system", Takahiro TADOKORO and others, 2015 Annual Meeting of the Atomic Energy Society of Japan Proceedings, Lecture No. 117, issued on Mar. 5, 2015

SUMMARY OF INVENTION

Technical Problem

In the radiation therapy apparatuses respectively disclosed in JP-A-7-303710, JP-A-2000-56381, and JP-A-2015-157003, body motion due to respiration is measured by using an ultrasonic tomographic apparatus and a probe, a respiration sensor, an infrared light emitting diode, and a semiconductor position detection element, and a light emitting diode (or an LED light reflection member) and a camera, and radiation is applied to an affected part of a patient in accordance with a cycle of the measured body motion. Thus, in order to perform radiation respiration synchronized irradiation, the above-described apparatus measuring body motion due to respiration is required to be provided.

As disclosed in JP-A-2001-56381, and "Bragg Curve Measurement in Near-Infrared Single Photon Counting Mode", Katsunori UENO and others, the 110th Japanese Society of Health and Medical Sociology, Vol. 35, Supplement No. 3 (September, 2015), page 77, the radiation detector is inserted into the body of a patient, and thus a dose applied to an affected part can be measured with high accuracy.

The inventors aim to realize a radiation therapy apparatus in which the accuracy of measurement of a dose applied to an affected part by inserting a radiation detector into the body, and respiratory synchronization control for performing respiration synchronized irradiation on a radiation irradiation target can be predetermined with higher accuracy.

A first object of the present invention is to provide a radiation therapy apparatus capable of improving the accuracy of a dose distribution in a radiation irradiation target irradiated with radiation.

A second object of the present invention is to provide a radiation therapy apparatus capable of measuring a dose in a radiation irradiation target with high accuracy, and thus performing respiration synchronized irradiation on the radiation irradiation target with higher accuracy.

Solution to Problem

According to a first aspect of the present invention for achieving the first object, there is provided a radiation therapy apparatus including:

a radiation generation device that generates radiation;

a radiation detector that is insertable into the body, and has a light emitting portion detecting the radiation and outputting photons;

a calculation device that obtains a counting rate of the photons output from the radiation detector, obtains a dose rate on the basis of the photon counting rate, and obtains a dose on the basis of the dose rate; and a first control device that performs any one of first control of either controlling the radiation generation device such that the dose obtained by the calculation device becomes a set dose or controlling the radiation generation device such that the dose rate obtained by the calculation device becomes a first set dose rate in feedback control, second control of either adjusting a shape of an opening of a variable collimator attached to an irradiation head provided in the rotation gantry such that the dose becomes the set dose or adjusting the shape of the opening of the variable collimator such that the dose rate becomes the first set dose rate, and third control of either adjusting a position of a bed supporting a radiation irradiation target such that the dose becomes the set dose or adjusting the position of the bed such that the dose rate becomes the first set dose rate.

According to a second aspect of the present invention for achieving the second object, there is provided a radiation therapy apparatus including:

a radiation generation device that generates radiation;

a radiation detector that is insertable into the body, and has a light emitting portion detecting the radiation and outputting photons;

a calculation device that obtains a counting rate of the photons output from the radiation detector, and obtains a dose rate on the basis of the photon counting rate; and a second control device that controls the radiation generation device such that a radiation irradiation target is irradiated with the radiation in a case where the dose rate obtained by the calculation device is equal to or lower than a second set dose rate in respiratory synchronization control, and the radiation irradiation target is stopped being irradiated with the radiation in a case where the dose rate exceeds the second set dose rate.

Advantageous Effects of Invention

According to the first aspect of the present invention, it is possible to improve the accuracy of a dose distribution in a radiation irradiation target irradiated with radiation.

According to the second aspect of the present invention, it is possible to measure the accuracy of a dose in a radiation irradiation target irradiated with radiation, and thus to perform respiration synchronized irradiation on the radiation irradiation target with higher accuracy.

DESCRIPTION OF EMBODIMENTS

Examples of the present invention will be described below.

Example 1

Figure 1:
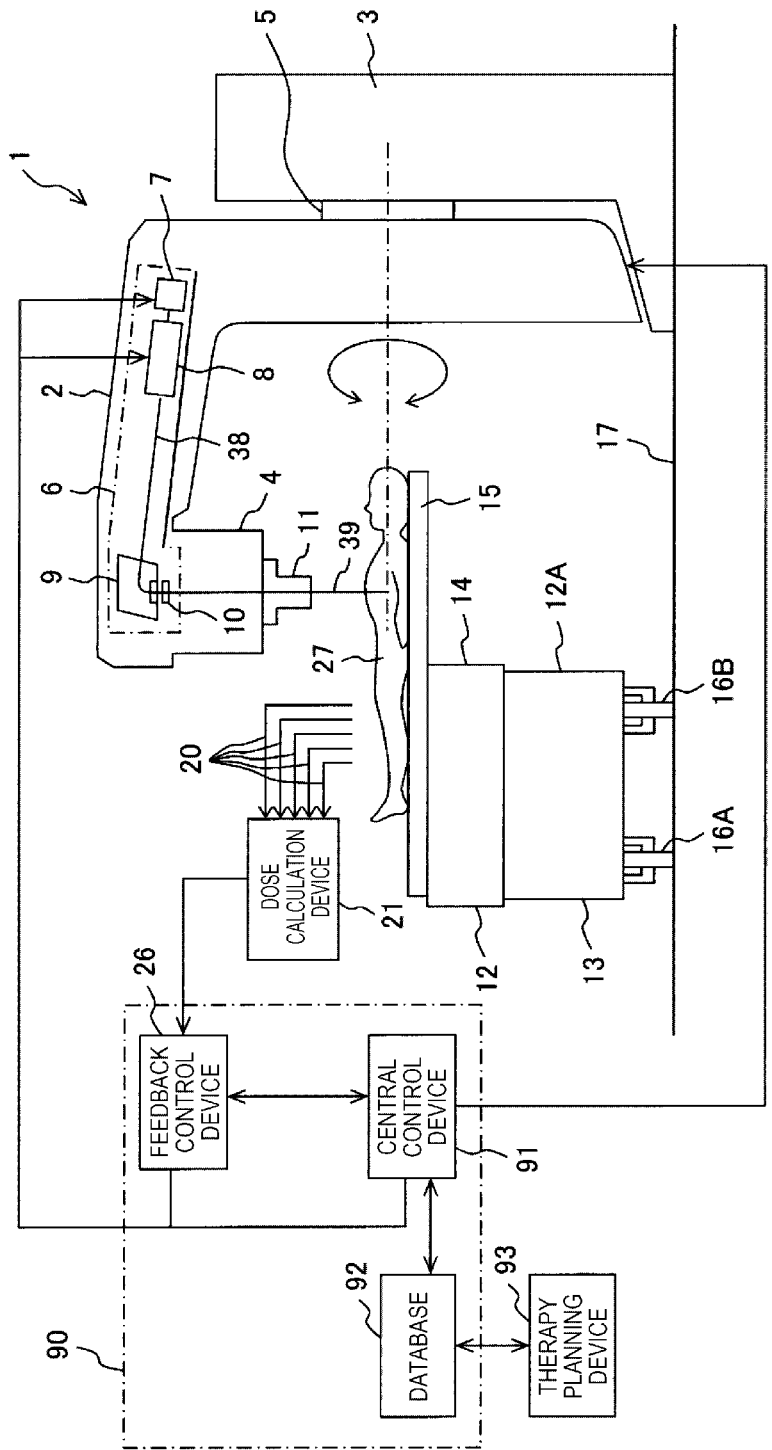
FIG. 1 is a configuration diagram of an X-ray therapy apparatus which is a radiation therapy apparatus of Example 1 which is one preferable example of the present invention.

A description will be made of a radiation therapy apparatus of Example 1 which one preferable example of the present invention with reference to FIGS. 1 and 2. A radiation therapy apparatus of the present example is an X-ray therapy apparatus.

An X-ray therapy apparatus 1 of the present example includes a rotation gantry 2, a trestle 3, an irradiation head 4, an X-ray generation device (radiation generation device) 6, a variable collimator 11, a therapy table 12, a radiation detector 18, a dose calculation device 21, and a control system 90. The X-ray therapy apparatus 1 is provided on a floor 17 in a treatment room (not illustrated).

A rotation shaft 5 provided at the rotation gantry 2 is rotatably attached to the trestle 3 provided on the floor 17 of the treatment room, so as to be supported by the trestle 3. A motor (not illustrated) is installed in the trestle 3, and rotation of the motor is decelerated by a deceleration mechanism (not illustrated) installed in the trestle 3 so as to be delivered to the rotation shaft 5. The irradiation head 4 is provided at a distal end of an arm portion of the rotation gantry 2 so as to face a bed 15 which will be described later. The variable collimator 11 is attached to a front end of the irradiation head 4, and faces the bed 15. The X-ray generation device 6 is provided in the arm portion. The X-ray generation device 6 includes an electron beam generation portion (for example, an electron gun) 7, a linear accelerator 8, a deflection electromagnet 9, and a target 10. The electron beam generation portion 7 is connected to the linear accelerator 8. The deflection electromagnet 9 is disposed near the irradiation head 4 at the distal end of the arm portion. The target 10 faces the deflection electromagnet 9, and is disposed further toward the irradiation head 4 side than the deflection electromagnet 9.

The therapy table 12 is installed on the floor 17 of the treatment room, and includes drive mechanisms 12A and the bed 15. The drive mechanisms 12A include an X direction drive mechanism 13, a vertical direction drive mechanism 14, and a Y direction drive mechanism (not illustrated). The X direction drive mechanism 13 is installed so as to be movable along guide rails 16A and 16B installed on the floor 17 of the treatment room. The vertical direction drive mechanism 14 is installed on the X direction drive mechanism 13, and the Y direction drive mechanism is provided on the vertical direction drive mechanism 14. The bed 15 is installed on the Y direction drive mechanism. The Y direction drive mechanism moves the bed 15 in an axial direction of the rotation shaft 5. The X direction drive mechanism 13 moves the bed 15 in a direction orthogonal to a movement direction of the Y direction drive mechanism. The vertical direction drive mechanism 14 moves the bed 15 in a vertical direction.

Figure 3:
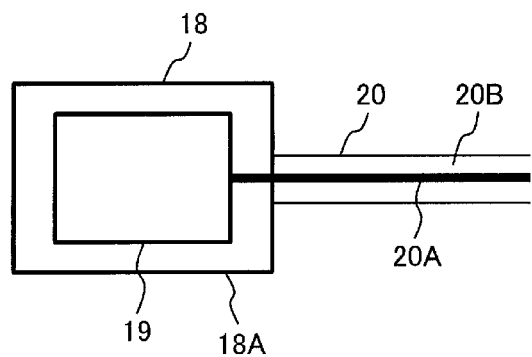
FIG. 3 is a configuration diagram illustrating details of the radiation detector illustrated in FIG. 2.

As illustrated in FIG. 3, the radiation detector 18 includes a cover 18A and a light emitting portion 19. The entire surface of the light emitting portion 19 is covered with the cover 18A. The light emitting portion 19 is made of a radiation light emitting material which generates light with the intensity depending on an amount of incident radiation (for example, an X-ray). The radiation light emitting material contains, for example, at least one species of rare earth elements such as ytterbium, neodymium, cerium, and praseodymium in a base material such as transparent yttrium aluminum garnet (YAG). As mentioned above, since the radiation light emitting material contains at least one rare earth element, it is possible to improve linearity between a dose rate of radiation incident to the light emitting portion 19 and the intensity of light emitted from the light emitting portion 19 due to the incident radiation. Thus, the radiation detector 18 can more accurately measure a dose rate of radiation even if radiation with a high dose rate is incident. In the present example, the light emitting portion 19 is made of, for example, Nd:YAG (YAG containing neodymium).

Instead of Nd:YAG, the light emitting portion 19 may employ any of NdCe:YAG, Yb:YAG, Yb:LuAG, Nd:YVO$_4$, Tm:YVO$_4$, Tm:YAG, Yb:YVO$_4$, Eu:YVO$_4$, Nd:GdVO$_4$, Ce:LiSAF, Ce:LiCAF, Ce:LiSGaF, Nd:YLF, Pr:YLF, Er:YLF, Ho:YLF, Yb:KGW, and Nd:KGW. Each of such all materials contains at least one rare earth element.

The cover 18A transmits radiation (for example, an X-ray) therethrough, but is made of a material having light blocking property of blocking external light from being incident to the light emitting portion 19. A material used in the cover 18A is, for example, aluminum. The cover 18A made of a light blocking material reflects the light generated by the light emitting portion 19 toward the light emitting portion 19. When it is taken into consideration that the radiation detector 18 is inserted into the body, an outer surface of the cover 18A brought into contact with an internal organ is required to be made of a stable and harmless material.

Figure 4:
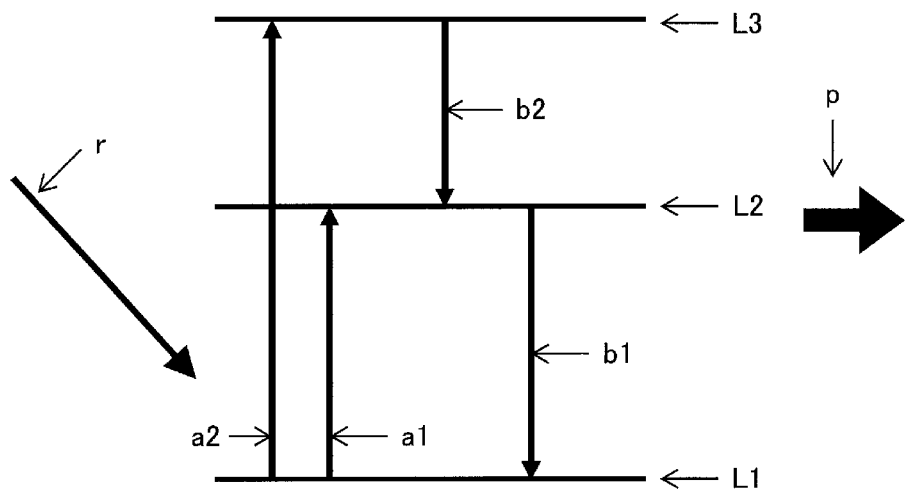
FIG. 4 is an explanatory diagram illustrating a process in which a photon (light) is generated by radiation incident to a light emitting portion of the radiation detector illustrated in FIG. 3.

In the light emitting portion 19 made of Nd:YAG, a description will be made of a process in which a photon p is generated when radiation is incident, with reference to FIG. 4. In a case where radiation r is incident to the light emitting portion 19, a rare earth atom in the light emitting portion 19 is caused to transition to an excitation state (for example, energy levels L2 and L3) in which energy is higher, by energy of the radiation r (refer to arrows a1 and a2 in FIG. 4). On the other hand, when the rare earth atom having high energy in the excitation state (for example, the energy levels L2 and L3) transitions to an excitation state (for example, the energy level L2) or a base state (for example, an energy level L1) in which energy is lower (refer to arrows b2 and b1 in FIG. 4), the photon p having energy corresponding to difference in the energy is generated.

As illustrated in FIG. 3, an optical fiber 20 has a core 20A located at the center, and a clad 20B surrounding the core 20A. In a case where the optical fiber 20 is actually used, an outer surface of the clad 20B is coated with, for example, PVC. The core 20A is connected to the light emitting portion 19. The core 20A is made of, for example, quartz or plastic.

Figure 5:
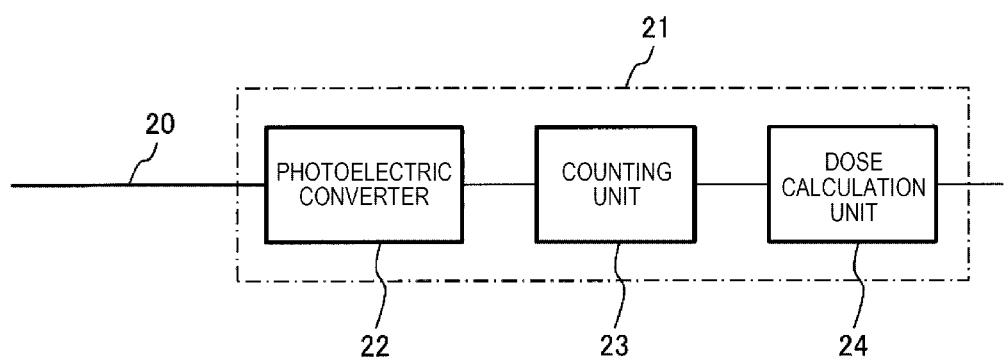
FIG. 5 is a configuration diagram illustrating details of a dose calculation device illustrated in FIG. 1.

The optical fiber 20 is connected to the dose calculation device 21. As illustrated in FIG. 5, the dose calculation device 21 includes a photoelectric converter 22, a counting unit 23, and a dose calculation unit 24. The optical fiber 20 is connected to the photoelectric converter 22. As the photoelectric converter 22, a photomultiplier tube or a photodiode (for example, an avalanche photodiode) is used. The photoelectric converter 22 is a converter which transmits a single electric pulse for each photon p which is input through the optical fiber 20. Light (photon) can be converted into an electric pulse of which a current is amplified by using the photoelectric converter 22. The counting unit 23 is connected to the photoelectric converter 22, and the dose calculation unit 24 is connected to the counting unit 23. The counting unit 23 is connected to the photoelectric converter 22 via an amplifier (not illustrated) which amplifies an electric pulse. The counting unit 23 counts input electric pulses, so as to obtain a counting rate of the electric pulses.

Figure 6:
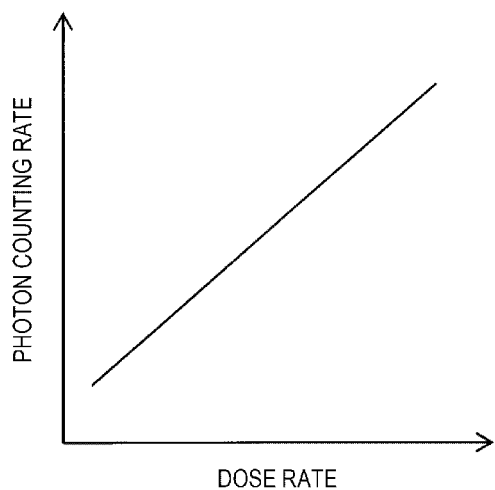
FIG. 6 is a characteristic diagram illustrating a relationship between a dose rate and a photon counting rate.

The dose calculation unit 24 stores, in a memory (not illustrated), a data table in which a dose rate of radiation and the number of photons (hereinafter, referred to as a photon counting rate) per unit time emitted in the light emitting portion 19, illustrated in FIG. 6, are correlated with each other. The data table substantially correlates a dose rate of radiation with an electric pulse output from the photoelectric converter 22. As illustrated in FIG. 6, a dose rate of radiation and a photon counting rate have a proportional relationship. The inventors have found that a dose rate of radiation incident to the light emitting portion 19 of the radiation detector 18 and a counting rate of photons (light) emitted in the light emitting portion 19 have a proportional relationship in a wide range, through tests. The proportional relationship between a dose rate of radiation and a photon counting rate is also established for the radiation detector 18 having the light emitting portion 19 made of the above-described materials other than Nd:YAG, containing rare earth elements other than Nd:YAG.

It is well known that there is a correspondence relationship on a one-to-one basis between a photon counting rate and a counting rate of electric pulses, and thus a counting rate of electric pulses output from the counting unit 23 can be converted into a dose rate of radiation incident to the radiation detector 18 by using the characteristics illustrated in FIG. 6. The correspondence relationship between a dose rate of radiation and a photon counting rate differs depending on a size, a shape, and a material of the light emitting portion 19 used in the radiation detector 18, and a thickness and a length of the optical fiber 20, and thus a correspondence relationship between a dose rate of radiation and a photon counting rate may be created as a data table according to the light emitting portion 19 and the optical fiber 20 to be used. Consequently, even in a case where sizes, shapes, and materials of the light emitting portion 19 and thicknesses and lengths of the optical fiber 20 are different from each other, a counting rate of electric pulses obtained in the counting unit 23 can be converted into a dose rate of radiation.

The dose calculation unit 24 includes a timer (not illustrated). The timer is activated in response to input of an activation control command output from a central control device 91, and is stopped in response to input of a stop control command from a feedback control device 26 which will be described later. Thus, the timer measures a time period from the input of the activation control command to the input of the stop control command, that is, a radiation irradiation time for an affected part. The dose calculation unit 24 calculates a dose applied to the affected part by using the obtained dose rate and the measured radiation irradiation time. The timer measuring an irradiation time may be provided in the central control device 91 instead of the dose calculation unit 24.

The control system 90 includes the feedback control device (first control device) 26, the central control device 91, and a database 92. The central control device 91 is connected to the feedback control device 26. The database 92 is connected to the central control device 91 and a therapy planning device 93. The dose calculation device 21, specifically, the dose calculation unit 24 is connected to the feedback control device 26.

A description will be made of cancer therapy of a patient using the X-ray therapy apparatus 1. A patient 27 subjected to the therapy is placed on the bed 15 of the therapy table 12 (refer to FIGS. 1 and 2). As schematically illustrated in FIG. 2, a plurality of radiation detectors 18 are inserted into the body of the patient 27 on the bed 15. The radiation detectors 18 are installed in an endoscope, and are inserted up to a position near an affected part by being inserted into any of the esophagus, the stomach, and the duodenum through, for example, the mouth or the nostrils, or into the large intestine through the anus. The radiation detectors 18 may be installed in a catheter, and may be inserted up to a position near an affected part by being inserted into a body cavity or an internal organ of the patient. The number of radiation detectors 18 inserted into the body may be minimally one, but a dose distribution in the vicinity of an affected part irradiated with an X-ray can be measured by inserting a plurality of radiation detectors 18 in the body. It can be expected that, as the number of radiation detectors 18 inserted into the body is increased, the accuracy of X-ray irradiation for an affected part is improved, but the number and disposition positions in the body of inserted radiation detectors 18 may be determined by taking into consideration a size of an X-ray irradiation region in the body, position accuracy required to dispose the radiation detectors 18 in the body, and invasiveness of when the radiation detectors 18 are inserted into the body. An outer diameter of each of the radiation detectors 18 and the optical fibers 20 is about 1 mm.

The bed 15 is moved by driving the drive mechanisms 12A, and thus the affected part of the patient 27 is positioned at a central line of the irradiation head 4. In other words, the X direction drive mechanism 13 is moved along the guide rails 16A and 16B, and thus the affected part of the patient 27 on the bed 15 is aligned with the axial center of the rotation shaft 5 in the X direction. The vertical direction drive mechanism 14 is driven, and thus the affected part of the patient 27 on the bed 15 is aligned with the axial center of the rotation shaft 5 in the vertical direction. The Y direction drive mechanism is driven such that the bed 15 is moved in the axial direction of the rotation shaft 5, and thus the affected part is aligned with the central line of the irradiation head 4.

Before the patient 27 is placed on the bed 15, therapy planning for the affected part of the patient 27 is performed. In this therapy planning, therapy plan information such as an X-ray irradiation direction, a shape of the affected part viewed from the irradiation direction, a set dose for the affected part, and intensity and energy of an X-ray is created by using the therapy planning device 93. The created therapy plan information is input to the database 92 from the therapy planning device 93, and is stored in the database 92.

The central control device 91 reads the therapy plan information of the patient subjected to the therapy from the database 92, and stores the therapy plan information in a memory (not illustrated) of the central control device 91. Since the central line of the irradiation head 4 is aligned with a certain single X-ray irradiation direction defined in the therapy plan, the central control device 91 outputs a rotation control command to the rotation gantry 2 so as to rotate the rotation gantry 2. The motor in the trestle 3 is driven in response to the rotation control command such that the rotation shaft 5 is rotated, and thus the rotation gantry 2 is rotated. When the central line of the irradiation head 4 is located in the X-ray irradiation direction, the motor is stopped, and thus rotation of the rotation gantry 2 is stopped.

The central control device 91 controls the variable collimator 11, and thus aligns a shape of an opening of the variable collimator 11 with a shape of the affected part viewed from the X-ray irradiation direction on the basis of the therapy plan information. The central control device 91 outputs an activation control command to the electron beam generation portion 7.

In the electron beam generation portion 7, a voltage is applied to a filament on the basis of the activation control command, and electrons are emitted from the heated filament. A plurality of emitted electrons form an electron beam, and are incident to the linear accelerator 8. The electron beam is accelerated by the linear accelerator 8, and thus becomes an electron beam having predetermined energy. An electron beam 38 emitted from the linear accelerator 8 has predetermined energy, and collides with the target 10 as a result of an advancing direction thereof being bent by the deflection electromagnet 9. The electron beam 38 collides with the target 10, and thus an X-ray 39 is emitted from the target 10. The X-ray 39 advances toward the affected part of the patient 27 on the bed 15 along the central line of the irradiation head 4, and is emitted from the irradiation head 4 so as to be applied to the affected part through the opening of the variable collimator 11.

The affected part is irradiated with the X-ray 39, and thus each radiation detector 18 inserted into the body detects the X-ray 39. The applied X-ray 39 is incident to the light emitting portion 19 of the radiation detector 18. The periphery of the light emitting portion 19 is surrounded by the cover 18A, and thus external light is blocked by the cover 18A and does not reach the light emitting portion 19. Thus, the photon p generated in the light emitting portion 19 is input to the photoelectric converter 22 through the core 20A of the optical fiber 20. The radiation detector 18 having the light emitting portion 19 made of Nd:YAG outputs a plurality of photons corresponding to total energy of a plurality of X-rays which are incident at one time, one by one with the time delay.

A single photon which is input to the photoelectric converter 22 is converted into a single electric pulse. Thus, the photoelectric converter 22 sequentially outputs electric pulses of the number corresponding to the number of input photons. The counting unit 23 to which the electric pulses are input counts the number of input electric pulses, and obtains the number of electric pulses per unit time, that is, a counting rate of the electric pulses. The obtained counting rate of the electric pulses is input to the dose calculation unit 24 from the counting unit 23.

The counting rate of the electric pulses corresponds to a photon counting rate on a one-to-one basis, and thus the dose calculation unit 24 converts the counting rate of the electric pulses into a dose rate by using the information of the data table (characteristics in FIG. 6) stored in the memory. The dose calculation unit 24 multiplies an X-ray irradiation time measured by the timer provided in the dose calculation unit 24 by the obtained dose rate, so as to obtain a dose applied to the affected part. The dose is a dose at an insertion position of the radiation detector 18 inserted into the body of the patient, and is obtained for each radiation detector 18 inserted into the body. The dose at each insertion position of the radiation detector 18, obtained by the dose calculation unit 24, is input to the feedback control device 26 which performs feedback control.

Figure 9:
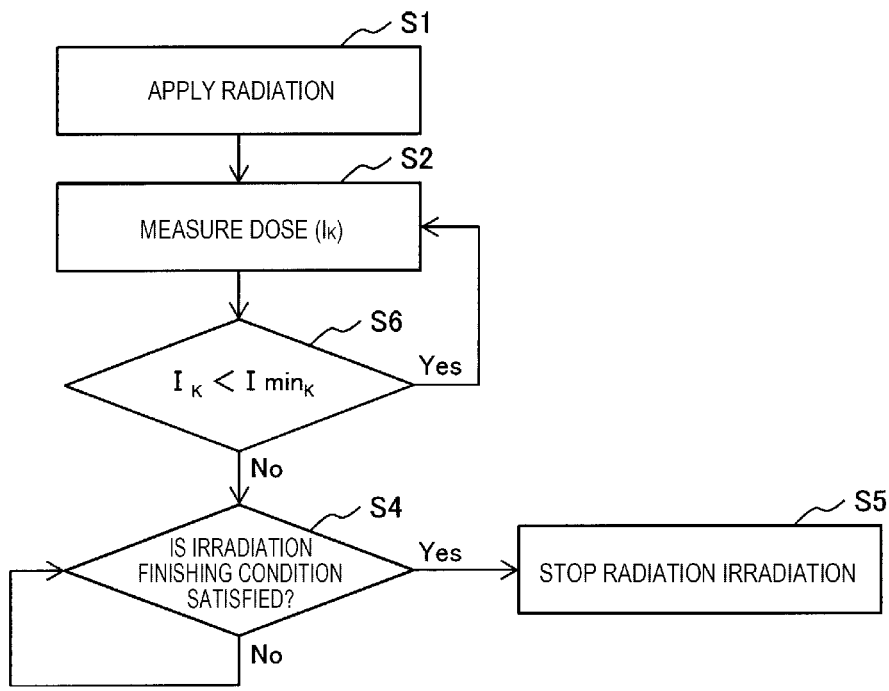
FIG. 9 is a flowchart illustrating another example of control performed by the feedback control device of the X-ray therapy apparatus.
Figure 10:
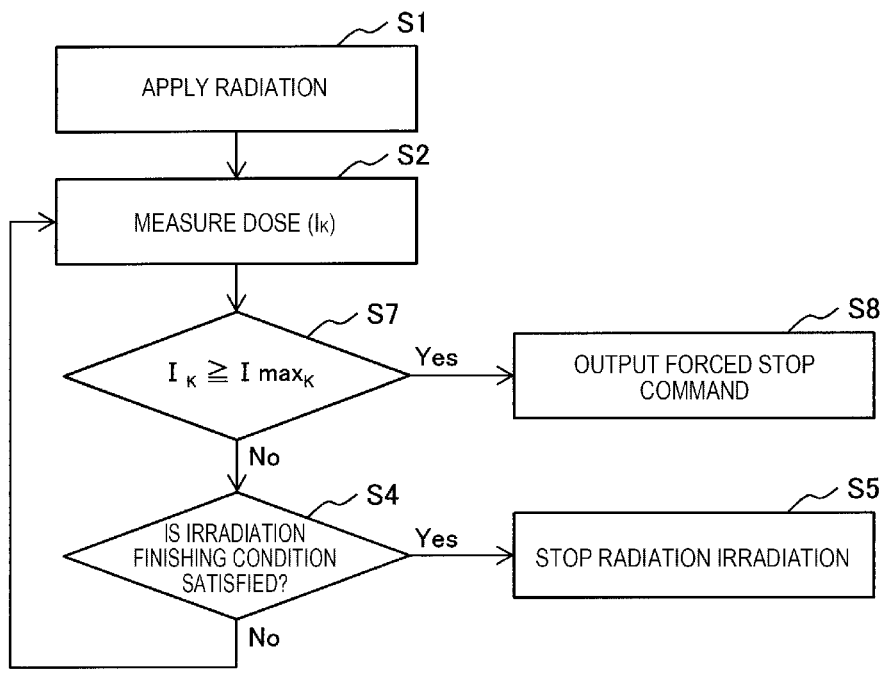
FIG. 10 is a flowchart illustrating still another example of control performed by the feedback control device of the X-ray therapy apparatus.
Figure 11:
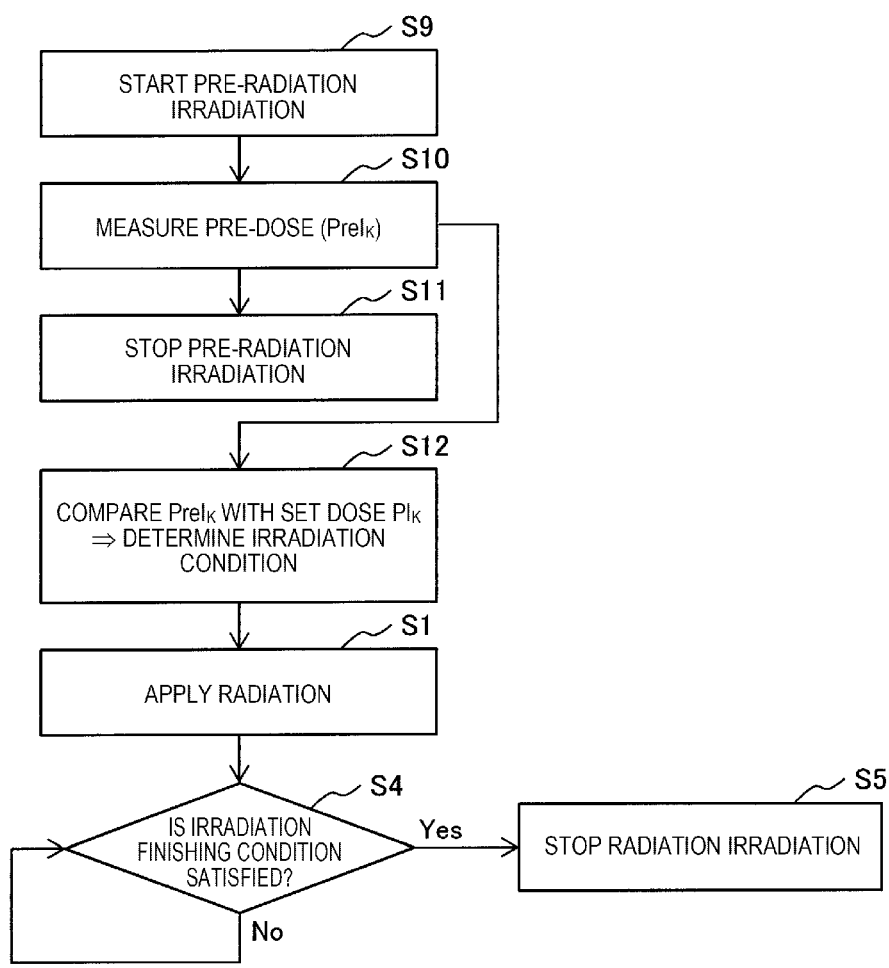
FIG. 11 is a flowchart illustrating still another example of control performed by the feedback control device of the X-ray therapy apparatus.

A description will be made of feedback control performed by the feedback control device 26. The feedback control device 26 performs feedback control on the basis of a dose (or a dose rate) obtained by the dose calculation unit 24 in respective processes in steps S3 to S5 illustrated in FIG. 7. The feedback control is performed when an X-ray is applied to the affected part of the patient 27 lying on the bed 15 in a certain irradiation direction. Feedback control illustrated in FIGS. 9 to 11 is also similarly performed.

Radiation is applied to the affected part (step S1). The process in step S1 is already performed before the feedback control device 26 performs feedback control. As described above, the process in step S1 is performed by the central control device 91 outputting an activation control command to the electron beam generation portion 7. Consequently, the electron beam 38 collides with the target 10, and thus the generated X-ray 39 is applied to the affected part of the patient 27 on the bed 15.

A dose is measured (step S2). The process in step S2 is also already performed before the feedback control device 26 performs feedback control. As described above, the process in step S2 of measuring a dose is a process in which the dose calculation unit 24 obtains a dose rate on the basis of a detection signal of the X-ray 39 detected by the radiation detector 18 inserted into the body of the patient 27, and obtains a dose by using the dose rate. As mentioned above, in step S2, the dose calculation unit 24 obtains a dose $I_k$. Here, k indicates a number of the radiation detector 18, and is an integer of 1 to N (where N is the number of radiation detectors 18 inserted into the body). The number of radiation detectors 18 may be one, and may be plural. Since a dose rate is obtained when a dose is obtained, in step S2, a dose rate $R_k$ obtained for each radiation detector 18 is obtained.

In a case where the obtained dose $I_k$ does not become the set dose $PI_k$ defined in the therapy plan, an X-ray intensity (irradiation condition) is changed such that a dose distribution defined in the therapy plan is obtained (step S3) The feedback control device 26 receives the dose $I_k$ obtained by the dose calculation unit 24, and compares the dose $I_k$ with the set dose $PI_k$. In a case where it is determined that the dose $I_k$ does not become the set dose $PI_k$, the feedback control device 26 controls the electron beam generation portion 7 through feedback control such that the set dose distribution defined in the therapy plan is obtained. Specifically, a voltage to be applied to the filament of the electron beam generation portion 7 is changed (increased or decreased) such that the dose distribution is obtained, and the intensity of an electron beam, that is, the intensity of an X-ray is controlled. The set dose $PI_k$ is defined in the therapy plan, and is stored in the memory (not illustrated) of the central control device 91 from the database 92.

In step S3, in a case where a predetermined dose distribution cannot be obtained even if an X-ray intensity is changed such that the dose distribution defined in the therapy plan is obtained, irradiation with the X-ray on the affected part is stopped, and second therapy planning is performed. In the second therapy planning, a new set dose distribution is obtained by using the dose $I_k$ obtained by the dose calculation unit 24. A new set dose $NPI_k$ corresponding to the new set dose distribution is stored in the memory of the central control device 91.

It is determined whether or not an irradiation finishing condition is satisfied (step S4). The feedback control device 26 determines whether or not the irradiation finishing condition is satisfied, that is, whether or not the dose $I_k$ becomes the set dose $PI_k$. As described above, in a case where the second therapy planning is performed, and the new set dose $NPI_k$ is set, it is determined whether or not the dose $I_k$ becomes the new set dose $NPI_k$. When the dose $I_k$ becomes the set dose $PI_k$ (or the new set dose $NPI_k$), the feedback control device 26 outputs a stop control command to the electron beam generation portion 7. As a result, generation of an electron beam in the electron beam generation portion 7 is stopped, and irradiation with the X-ray 39 on the affected part is stopped (step S5). In a case where it is determined that the irradiation condition is not satisfied in step S4, irradiation with the X-ray 39 is continuously performed on the affected part, and the respective processes in steps S3 and S4 are repeatedly performed in the feedback control device 26.

In a case where the obtained dose $I_k$ does not become the set dose $PI_k$, an X-ray intensity (irradiation condition), specifically, the intensity of an electron beam is controlled such that a dose distribution defined in the therapy plan is obtained, and thus an appropriate dose distribution can be obtained through irradiation with an X-ray on the affected part. Since the intensity of an X-ray is controlled by adjusting a voltage to be applied to the filament of the electron beam generation portion 7 through feedback control, control thereof is simpler than control of other parameters.

In a case where irradiation with an X-ray on the affected part in a certain single irradiation direction, the central control device 91 rotates the rotation gantry 2 such that the central line of the irradiation head 4 matches another single X-ray irradiation direction. Thereafter, as described above, irradiation with an X-ray is also performed on the affected part in another single X-ray irradiation direction. As mentioned above, irradiation with an X-ray on the affected part is performed in a plurality of X-ray irradiation directions defined in the therapy plan, and consecutive irradiation in which an X-ray is applied from the periphery of the affected part is performed. In a case where irradiation with an X-ray on the affected part from all of the X-ray irradiation directions is finished, therapy of the affected part using X-ray irradiation is finished.

The feedback control device 26 may perform the feedback control by using the dose rate $R_k$ instead of the dose $I_k$. In a case of using the dose rate $R_k$, a set dose rate (first set dose rate) $PR_k$ is used instead of the set dose $PI_k$. The set dose rate (first set dose rate) $PR_k$ is a set dose rate used for feedback control. In this feedback control, the respective processes in steps S2 to S4 are changed as follows. The step S2 (measurement of a dose) is changed to step S2 (measurement of a dose rate). In step S2 (measurement of a dose rate), obtaining a dose by using an obtained dose rate, performed in the above step S2 (measurement of a dose), is not performed, and the dose rate $R_k$ is obtained on the basis of a detection signal of an X-ray. In step S3, in a case where the obtained dose rate $R_k$ does not become the set dose rate $PR_k$ defined in the therapy plan, an X-ray intensity (irradiation condition) is changed such that a dose distribution rate defined in the therapy plan is obtained. In step S4, it is determined whether or not the dose rate $R_k$ becomes the set dose rate $PR_k$. When the dose rate $R_k$ becomes the set dose rate $PR_k$, a stop control command is output to the electron beam generation portion 7, and irradiation with an X-ray on the affected part is stopped (step S5). The X-ray irradiation stop is in an unexpected state, and X-ray therapy is required to be performed again.

In the present example, effects of (1) to (3) described below can be achieved.

(1) Since the radiation detector 18 is inserted into the body, doses respectively applied to an affected part irradiated with an X-ray and a normal cell in the vicinity of the affected part can be measured with high accuracy compared with a case where the radiation detector is disposed outside the body.

(2) Since the light emitting portion 19 of the radiation detector 18 used in the present example is made of, for example, a radiation light emitting material containing a rare earth element in a base material such as transparent YAG, a counting rate of photons output from the light emitting portion 19 of the radiation detector 18 is proportional to a dose rate in a wide range, for example, a dose rate in a range of a dose rate of $1.0 \times 10^{-2}$ to $1.0 \times 10^5$ Gy/h as illustrated in FIG. 6. The light emitting portion 19 can output a plurality of photons corresponding to total energy of a plurality of X-rays which are incident at one time, one by one with the time delay. Thus, each photon can be converted into each electric pulse, and thus a dose rate can be obtained with high accuracy. The accuracy of a dose obtained on the basis of the dose rate is also improved.

(3) According to the present example, it is determined whether or not the dose $I_k$ at each of positions where all of the radiation detectors 18 are disposed in the body becomes the set dose $PI_k$, that is, an internal dose distribution in the vicinity of an affected part due to X-ray irradiation is a set dose distribution, and, in a case where the internal dose distribution does not become the set dose distribution, an X-ray intensity is controlled through feedback control using the feedback control device 26. Therefore, the internal dose distribution can be matched with the set dose distribution with high accuracy. In other words, it is possible to improve the accuracy of a dose distribution in the body irradiated with an X-ray.

Energy of an X-ray may be controlled instead of controlling an X-ray intensity through feedback control using the feedback control device 26. A description will be made of the feedback control of energy of an X-ray.

In a case where it is determined that the dose $I_k$ does not become the set dose $PI_k$ in step S3, the feedback control device 26 controls the linear accelerator 8 through feedback control such that a set dose distribution defined in the therapy plan is obtained. A pair of facing electrodes is disposed in a plurality at a predetermined interval in an advancing direction of an accelerated electron beam in the linear accelerator 8. High frequency voltages are applied to the electrodes adjacent to each other in the advancing direction so as to be charged to different polarities, and thus an electron beam is accelerated. The applied high frequency voltages are controlled by the feedback control. In a case where the applied high frequency voltages are increased, an electron beam is accelerated, energy of the electron beam is increased, and thus energy of an X-ray generated in the target is also increased. Energy of an X-ray can be controlled through feedback control using the feedback control device 26.

As mentioned above, since energy of an X-ray is controlled through feedback control, an internal dose distribution can be matched with a set dose distribution with high accuracy.

Figure 7:
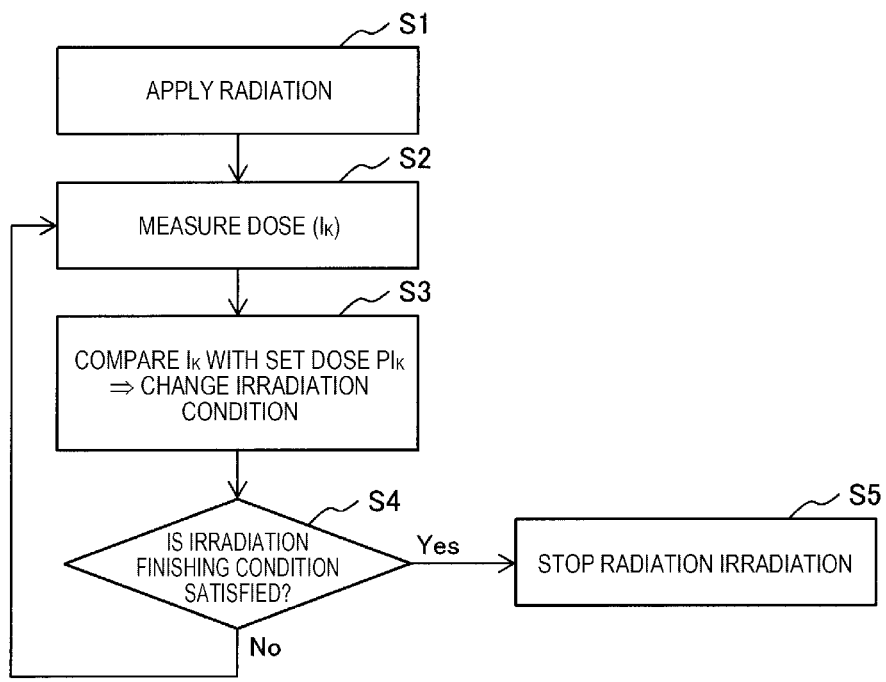
FIG. 7 is a flowchart illustrating an example of control performed by a feedback control device of the X-ray therapy apparatus illustrated in FIG. 1.

The feedback control device 26 may control respective processes in steps S6, S4, and S5 illustrated in FIG. 9 instead of the respective processes in steps S3, S4, and S5 illustrated in FIG. 7.

It is determined whether or not the obtained dose $I_k$ is smaller than the minimum dose $Imin_k$ defined in the therapy plan (step S6). The minimum dose $Imin_k$ is stored in the memory (not illustrated) of the central control device 91 from the database 92. Before the step S6 is performed, the respective processes in steps S1 and S2 are performed. The feedback control device 26 receives the dose $I_k$ obtained by the dose calculation unit 24, and compares the dose $I_k$ with the minimum dose $Imin_k$ defined in advance in the therapy plan. In a case where it is determined that the dose $I_k$ is smaller than the minimum dose $Imin_k$, the feedback control device 26 continuously performs irradiation with an X-ray on the affected part under the current irradiation condition, and measures the dose $I_k$ in step S2.

In a case where the feedback control device 26 determines, in step S6, that the dose $I_k$ is not smaller than the minimum dose $Imin_k$, that is, the dose $I_k$ is equal to or larger than the minimum dose $Imin_k$, the feedback control device 26 performs a determination in the above step S4. In a case where the feedback control device 26 determines that an irradiation finishing condition is satisfied, that is, the dose $I_k$ becomes the set dose $PI_k$, the feedback control device 26 outputs a stop control command to the X-ray generation device 6, specifically, the electron beam generation portion 7, and thus irradiation with an X-ray on the affected part is stopped (step S5). In a case where it is determined that the irradiation condition is not satisfied in step S4, irradiation with an X-ray on the affected part is continuously performed, and the respective processes in steps S6 and S4 are repeatedly performed in the feedback control device 26.

The respective processes in steps S6 and S4 are performed, step S5 is performed in a case where a determination result in step S4 is Yes, and thus it is possible to perform control such that a required minimum dose is applied the affected part while monitoring a dose distribution in the affected part irradiated with an X-ray. Thus, a sufficient dose can be applied to an affected part for therapy of tumor, and thus the number of therapies using an X-ray can be reduced. A burden on the patient 27 can be reduced, and a therapy effect can be improved.

The feedback control device 26 may control respective processes in steps S7, S8, S4, and S5 illustrated in FIG. 10 instead of the respective processes in steps S3, S4, and S5 illustrated in FIG. 7.

It is determined whether or not the obtained dose $I_k$ is equal to or larger than the maximum dose $Imax_k$ defined in the therapy plan (step S7). The maximum dose $Imax_k$ is stored in the memory (not illustrated) of the central control device 91 from the database 92. Before the step S7 is performed, the respective processes in steps S1 and S2 are performed. The feedback control device 26 receives the dose $I_k$ obtained by the dose calculation unit 24, and compares the dose $I_k$ with the maximum dose $Imax_k$ defined in advance in the therapy plan. In a case where it is determined that the dose $I_k$ is smaller than the maximum dose $Imax_k$, the feedback control device 26 continuously performs irradiation with an X-ray on the affected part under the current irradiation condition, and proceeds to the process in step S4. In step S7, in a case where the feedback control device 26 determines that the dose $I_k$ is equal to or larger than the maximum dose $Imax_k$, the feedback control device 26 outputs a forced stop command to the electron beam generation portion 7 (step S8). In response to the forced stop command, generation of an electron beam in the electron beam generation portion 7 is emergently stopped, and thus irradiation with an X-ray on the affected part is emergently stopped.

In step S7, in a case where it is determined that the dose $I_k$ is smaller than the maximum dose $Imax_k$, the feedback control device 26 performs a determination in the above step S4. In a case where the feedback control device 26 determines that an irradiation finishing condition is satisfied, that is, the dose $I_k$ becomes the set dose $PI_k$, the feedback control device 26 outputs a stop control command to the electron beam generation portion 7, and thus irradiation with an X-ray on the affected part is stopped (step S5). In a case where it is determined that the irradiation condition is not satisfied in step S4, step S2 is performed such that irradiation with an X-ray on the affected part is continuously performed, and the respective processes in steps S7 and S4 are repeatedly performed in the feedback control device 26.

The respective processes in steps S7 and S4 are performed, step S8 is performed in a case where a determination result in step S7 is Yes, and step S5 is performed in a case where a determination result in step S4 is Yes. Therefore, particularly, it is determined whether or not the dose $I_k$ is equal to or larger than the maximum dose $Imax_k$, and thus it is possible to restrict an absorbed dose in a healthy cell in the vicinity of the affected part by irradiating the affected part with an X-ray while monitoring dose distributions in the vicinity of the affected part and in a normal organ or the like highly sensitive to the X-ray. Since an absorbed dose in a healthy cell in the vicinity of the affected part can be restricted, a side effect can be reduced, and thus it is possible to achieve high accuracy of X-ray therapy. Even in a case where a healthy organ highly sensitive to radiation is present near the affected part which is a therapy target, X-ray therapy of the affected part is possible, and thus an applicable range of the X-ray therapy, that is, the number of organs to which the X-ray therapy is applicable.

In a case where it is determined that the dose $I_k$ becomes the set dose $PI_k$ in step S4, the dose $I_k$ is stored in the memory of the central control device 91, and is reflected in a prior therapy plan for the next X-ray therapy of the patient 27.

In the feedback control illustrated in FIG. 10, the dose rate $R_k$ may be used instead of the dose $I_k$. In this feedback control, the respective processes in steps S2, S7, and S4 are changed as follows. The step S2 (measurement of a dose) is changed to step S2 (measurement of a dose rate) as described in the feedback control illustrated in FIG. 7. In step S7, in a case where it is determined that the dose rate $R_k$ is equal to or larger than the maximum dose rate $Rmax_k$, the feedback control device 26 outputs a forced stop command to the electron beam generation portion 7 (step S8). In a case where it is determined that the dose rate $R_k$ is smaller than the maximum dose rate $Rmax_k$, it is determined whether or not the dose rate $R_k$ becomes the set dose rate (first set dose rate) $PR_k$ in step S4. When the dose rate $R_k$ becomes the set dose rate $PR_k$, irradiation with an X-ray on the affected part is stopped (step S5).

The feedback control device 26 may control respective processes in steps S9 to S12, S4, and S5 illustrated in FIG. 11 instead of the respective processes in steps S3, S4, and S5 illustrated in FIG. 7.

Respective processes in steps S9 and S11 are performed by the central control device 91, step S10 is performed by the dose calculation device 21, and steps S12, S4, and S5 are performed by the feedback control device 26. In this feedback control, the respective processes in steps S9 to S12 are performed as pre-radiation irradiation before main irradiation (step S1) with an X-ray on the affected part for performing X-ray therapy of the affected part. In the pre-radiation irradiation, the intensity of an X-ray applied to the affected part is made lower than the intensity of an X-ray applied to the affected part in the main radiation irradiation.

Pre-X-ray irradiation is started (step S9). Before irradiation with an X-ray on the affected part in the pre-X-ray irradiation, as described above, the affected part of the patient 27 on the bed 15 is positioned at the central line of the irradiation head 4, the rotation gantry 2 is rotated such that the central line of the irradiation head 4 matches the X-ray irradiation direction, and an opening shape of the variable collimator 11 is controlled.

Thereafter, in order to perform the pre-X-ray irradiation before an X-ray is applied to the affected part for the purpose of X-ray therapy of the affected part, the central control device 91 outputs an activation control command to the electron beam generation portion 7. An electron beam from the electron beam generation portion 7 is incident to and accelerated in the linear accelerator 8, and becomes an electron beam having predetermined energy. The electron beam 38 emitted from the linear accelerator 8 collides with the target 10, and thus the X-ray 39 is emitted. The X-ray 39 having a low intensity is applied to the affected part of the patient 27 on the bed 15 through the irradiation head 4 and the variable collimator 11.

A pre-dose $PreI_k$ is measured (step S10). In the same manner as in the process in step S2, an output signal (photon) from the radiation detector 18 inserted into the body is subjected to processes in the photoelectric converter 22, the counting unit 23, and the dose calculation unit 24, and thus the pre-dose $PreI_k$ is obtained in the dose calculation unit 24.

The obtained pre-dose $PreI_k$ is compared with the set dose $PI_k$ defined in the therapy plan (step S12). In a case where the pre-dose $PreI_k$ does not become the set dose $PI_k$, an X-ray intensity (irradiation condition) for obtaining a dose distribution defined in the therapy plan is obtained. The feedback control device 26 receives the pre-dose $PreI_k$ obtained by the dose calculation unit 24, and compares the pre-dose $PreI_k$ with the set dose $PI_k$. In a case where it is determined that the pre-dose $PreI_k$ does not become the set dose $PI_k$, the feedback control device 26 obtains the intensity of an electron beam generated by the electron beam generation portion 7, causing the set dose distribution defined in the therapy plan to be obtained. The intensity of an electron beam corresponds to the intensity of an X-ray applied to the affected part. Thus, obtaining the intensity of an electron beam causing the set dose distribution defined the therapy plan to be obtained is to obtain the intensity of an X-ray causing the set dose distribution defined the therapy plan to be obtained. The feedback control device 26 stores a value (substantial irradiation condition) of a voltage to be applied to the filament of the electron beam generation portion 7, for obtaining the obtained intensity of an electron beam, in the memory.

The pre-X-ray irradiation is stopped (step S11). The irradiation condition is determined in step S10, and then the pre-X-ray irradiation is stopped. The pre-X-ray irradiation is stopped by the feedback control device 26 outputting a stop control command to the electron beam generation portion 7. In the pre-X-ray irradiation, a period from starting of X-ray irradiation in step S9 to stopping of X-ray irradiation in step S11 is, for example, at least 1 msec.

In a case where it is determined that the pre-dose $PreI_k$ does not become the set dose $PI_k$ in step S12, and the intensity of an electron beam, that is, the intensity of an X-ray causing the set dose distribution defined in the therapy plan to be obtained is not obtained, irradiation with the X-ray on the affected part is stopped, and second therapy planning is performed. In the second therapy planning, a new set dose distribution is obtained by using the pre-dose $PreI_k$ obtained by the dose calculation unit 24. In step S12 in pre-X-ray irradiation after the second therapy planning, the pre-dose $PreI_k$ obtained by the dose calculation unit 24 is compared with a new set dose $NPI_k$ corresponding to the new set dose distribution. In a case where pre-dose $PreI_k$ becomes the new set dose $NPI_k$, the intensity of an electron beam causing the new set dose distribution to be obtained is obtained, and a value (substantial irradiation condition) of a voltage to be applied to the filament of the electron beam generation portion 7, for obtaining the obtained intensity of an electron beam, is stored in the memory. The pre-X-ray irradiation is stopped in step S11.

After the pre-X-ray irradiation is finished, an X-ray is applied to the affected part in order to perform X-ray therapy of the affected part (step S). As described above, the process is performed by the central control device 91 outputting an activation control command to the electron beam generation portion 7, the electron beam 38 collides with the target 10, and thus the generated X-ray is applied to the affected part of the patient 27 on the bed 15. When an X-ray is applied to the affected part, in order to realize the X-ray intensity obtained in step S12, the feedback control device 26 controls a voltage to be applied to the filament of the electron beam generation portion 7 on the basis of the value of a voltage stored in the memory. As a result, the intensity of an electron beam generated from the electron beam generation portion 7 becomes the intensity of an electron beam causing the set dose distribution defined in the therapy plan to be obtained, and the electron beam having the intensity is accelerated in the linear accelerator 8, and thus the electron beam 38 is generated. The intensity of an X-ray generated as a result of the electron beam 38 colliding with the target 10 is also the intensity of an X-ray causing the set dose distribution defined in the therapy plan to be obtained. An X-ray having the intensity is applied to the affected part.

In the X-ray irradiation, when each radiation detector 18 inserted into the body of the patient 27 detects an applied X-ray, each radiation detector 18 outputs a photon. The photon is converted into an electric pulse in the photoelectric converter 22, and the counting unit 23 counts electric pulses, and outputs a counting rate of the electric pulses. The dose calculation unit 24 converts the counting rate of the electric pulses into a dose rate by using the information (FIG. 6) of the data table. The dose calculation unit 24 calculates a dose on the basis of the dose rate as described above.

The feedback control device 26 receives the dose $I_k$ at the position of each radiation detector 18, obtained by the dose calculation unit 24, and determines whether or not the dose $I_k$ becomes the set dose $PI_k$. As described above, the intensity of an electron beam generated from the electron beam generation portion 7 is controlled to become the intensity of an electron beam causing the set dose distribution defined in the therapy plan to be obtained, and thus the feedback control device 26 determines that the dose $I_k$ becomes the set dose $PI_k$. Thus, a voltage applied to the filament of the electron beam generation portion 7 is not changed, and irradiation with an X-ray is continuously performed on the affected part.

In a case where the feedback control device 26 determines that an irradiation finishing condition is satisfied, that is, the dose $I_k$ becomes the set dose $PI_k$, the feedback control device 26 outputs a stop control command to the electron beam generation portion 7, and thus irradiation with an X-ray on the affected part is stopped (step S5). In a case where it is determined that the irradiation condition is not satisfied in step S4, irradiation with an X-ray on the affected part is continuously performed, and the respective process in step S4 is repeatedly performed in the feedback control device 26.

By performing the respective processes in steps S9 to S12, before X-ray irradiation is performed in step S1, an irradiation condition (for example, the intensity of an X-ray) in this X-ray irradiation can be determined by referring to a measurement result of an actual internal dose distribution due to pre-X-ray irradiation. Thus, a calculation error of when a therapy plan regarding X-ray therapy of the patient 27 is made and a positioning error of an affected part can be corrected, and it is also possible to cope with secular changes of an affected part (organ) irradiated with an X-ray during therapy planning and during X-ray therapy. Therefore, it is possible to improve the accuracy of X-ray therapy.

The control performed by the feedback control device 26 illustrated in each of FIGS. 7 and 9 to 11 may be applied to Examples 2, 3, 4, and 7 which will be described later. In other words, the control is performed by a feedback control device 26, in Examples 2 and 7, performed by a feedback control device 26A in Example 3, and performed by a feedback control device 26B in Example 4.

Figure 8:
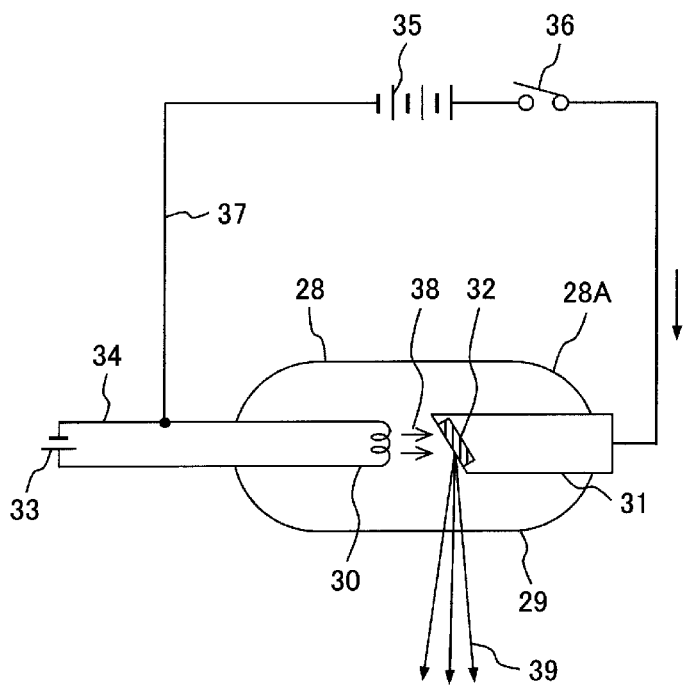
FIG. 8 is a configuration diagram illustrating an example of an X-ray tube device.

In the X-ray therapy apparatus 1, the X-ray generation device 6 is used, but an X-ray tube device may be used instead of the X-ray generation device 6. A description will be made of an X-ray tube device 28 which is an example of the X-ray tube device with reference to FIG. 8. The X-ray tube device 28 includes an anode 31 and a filament 30 disposed in a glass tube 28A. The inside of the glass tube 28A is a vacuum atmosphere, and the anode 31 faces the filament 30. A target 32 is attached to a surface of the anode 31 facing the filament 30. The target 32 is attached to the anode 31 in a tilted state. A power source 33 is connected to the filament 30 via a wire 34, and a high voltage power source 35 is connected to the anode 31 and the wire 34 via a wire 37. A switch 36 is provided at the wire 37.

The X-ray tube device 28 is installed at the arm portion of the rotation gantry 2 instead of the X-ray generation device 6 in the X-ray therapy apparatus 1. A current flows from the power source 33 to the filament 30 which is a cathode, and, in a case where the switch 36 is closed in a state in which the filament 30 is heated such that a high voltage from the high voltage power source 35 is applied between the filament 30 and the anode 31, an electron beam 38 generated from the filament 30 collides with the target 32 at a high speed. An X-ray 39 is generated from the target 32 due to the collision of the electron beam 38 with the target 32. The X-ray 39 advances along the central line of the irradiation head 4, and is emitted to the variable collimator 11 from the irradiation head 4 so as to be applied to the affected part of the patient 27 on the bed 15. Even if the X-ray tube device 28 is used as mentioned above, irradiation with an X-ray can be performed on the affected part.

Example 2

Figure 12:
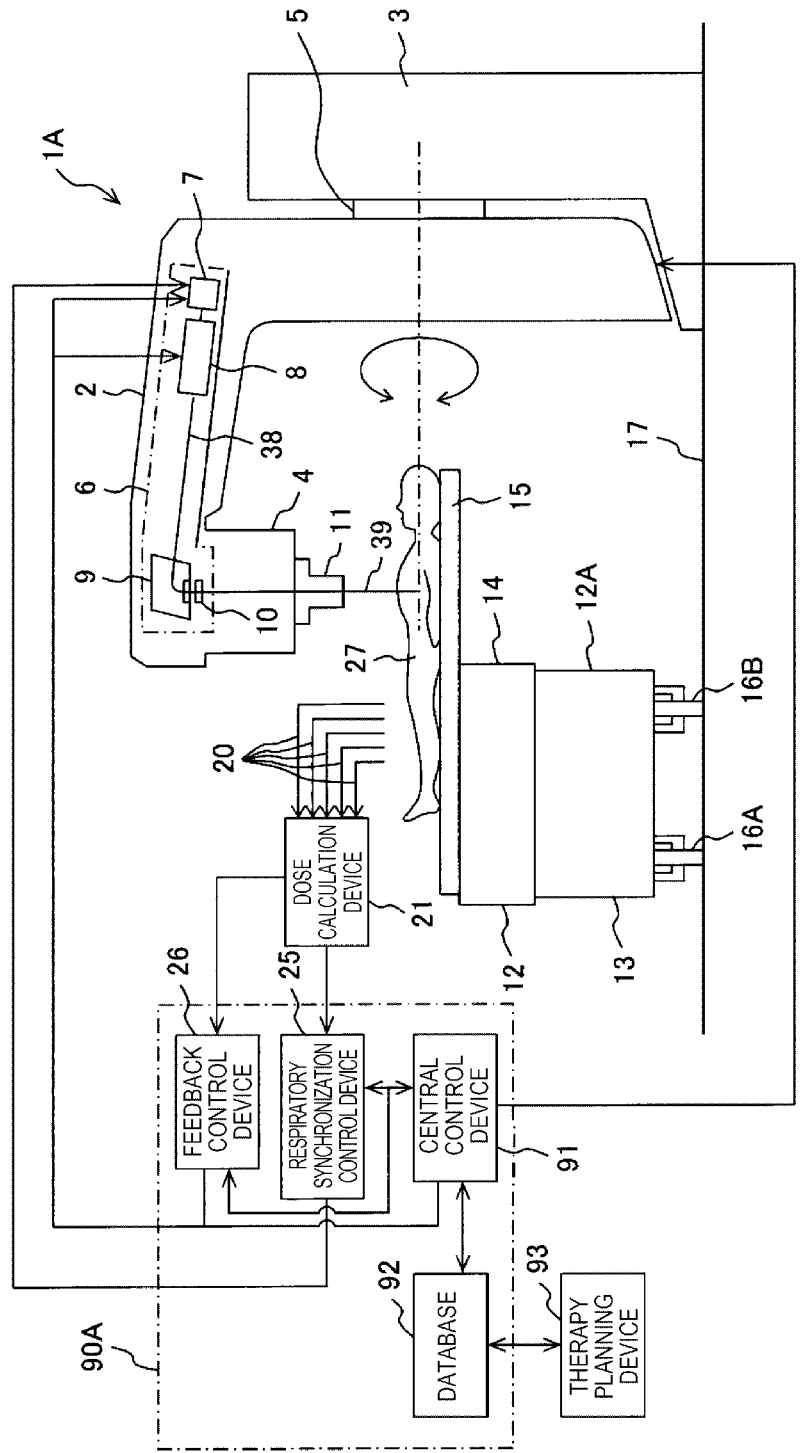
FIG. 12 is a configuration diagram of an X-ray therapy apparatus which is a radiation therapy apparatus of Example 2 which is another preferable example of the present invention.

A description will be made of a radiation therapy apparatus of Example 2 which is another preferable example of the present invention with reference to FIG. 12. The radiation therapy apparatus of the present example is an X-ray therapy apparatus.

An X-ray therapy apparatus 1A of the present example has a configuration in which the control system 90 is replaced with a control system 90A in the X-ray therapy apparatus 1 of Example 1. Other configurations of the X-ray therapy apparatus 1A are the same as those of the X-ray therapy apparatus 1. The control system 90A has a configuration in which a respiratory synchronization control device (second control device) 25 is added to the control system 90. Other configurations of the control system 90A are the same as those of the control system 90.

A description will be made of irradiation with an X-ray on an affected part of the patient 27 lying on the bed 15, using the X-ray therapy apparatus 1A.

In the same manner as in Example 1, the rotation gantry 2 is rotated such that the central line of the irradiation head 4 is aligned with a certain single X-ray irradiation direction defined in a therapy plan. A shape of an opening of the variable collimator 11 is adjusted, and then a plurality of electrons are emitted from the heated filament of the electron beam generation portion 7. The electrons become an electron beam having predetermined energy in the linear accelerator 8. The X-ray 39 is emitted from the target 10 as a result of the electron beam 38 emitted from the linear accelerator 8 colliding with the target 10. The X-ray 39 is emitted from the irradiation head 4 so as to be applied to the affected part through the opening of the variable collimator 11.

Each radiation detector 18 inserted into the body detects the X-ray 39, and outputs a plurality of photons one by one with the time delay. The dose calculation device 21 receives the photons, and obtains a dose rate and a dose at an insertion position of the radiation detector 18 inserted into the body for each radiation detector 18 in the same manner as in Example 1. The dose at each insertion position of the radiation detector 18, obtained by the dose calculation unit 24 of the dose calculation device 21, is input to the feedback control device 26 performing feedback control. The dose rate obtained by the dose calculation unit 24 is input to the respiratory synchronization control device 25 performing respiration synchronized irradiation control (respiratory synchronization control).

Figure 13:
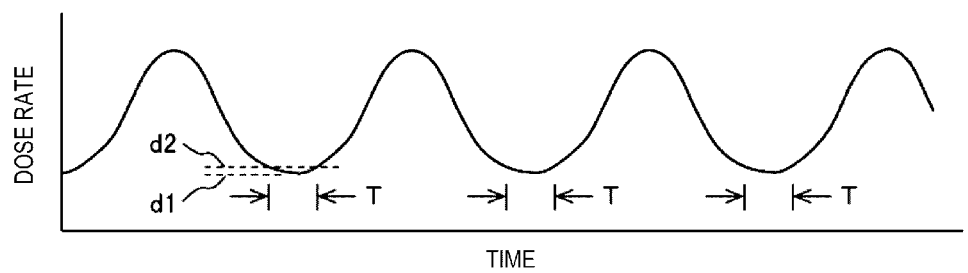
FIG. 13 is an explanatory diagram illustrating a cyclic change associated with body motion of a patient, of a dose rate obtained on the basis of a radiation detection signal detected by a radiation detector inserted into the body.

Irradiation with an X-ray on the affected part, synchronized with body motion due to respiration, is performed by the respiratory synchronization control device 25. A description will be made of irradiation with an X-ray synchronized with body motion. The dose rate obtained by the dose calculation unit 24 periodically changes due to body motion caused by respiration as illustrated in FIG. 13. The change in the dose rate is obtained on the basis of a signal output from a single radiation detector 18 inserted into the body. Dose rates obtained on the basis of signals output from the remaining radiation detectors 18 also periodically change. In the respiration, inspiration of inhaling air into the lung and expiration of exhaling air from the lung are repeated. Thus, a position where the radiation detector 18 inserted into the body is also changed according to body motion. A cycle of inspiration is about 1 second.

Since the position of the radiation detector 18 in the body comes close to the irradiation head 4 in an inspiration period, a dose rate obtained by the dose calculation unit 24 on the basis of an X-ray detected by the radiation detector 18 is increased. Since the position of the radiation detector 18 in the body becomes distant from the irradiation head 4 in an expiration period, a dose rate obtained by the dose calculation unit 24 on the basis of an X-ray detected by the radiation detector 18 is reduced. As a result, a dose rate obtained by the dose calculation unit 24 periodically changes due to body motion caused by respiration as illustrated in FIG. 13.

In JP-A-7-303710, respiration synchronized irradiation can be performed from the time of starting radiation irradiation on the basis of a respiration cycle phase which is measured in a state in which radiation is not applied to an affected part. However, in the present example, a dose rate cannot be obtained on the basis of a detection signal of an X-ray detected by the radiation detector 18 in a state in which an X-ray is not applied to an affected part. Thus, in a case where information (information indicating a change in a dose rate associated with body motion, corresponding to a cycle of inspiration of respiration) indicating a cyclic change in the dose rate associated with body motion of a patient, illustrated in FIG. 13, is to be created by using the dose rate obtained by the dose calculation unit 24 on the basis of an output signal from the radiation detector 18 in the body after X-ray irradiation on the affected part, at least the affected part is required to be irradiated with an X-ray for 4 or 5 seconds. However, in a case where the affected part is irradiated with an X-ray for 4 seconds, a dose in the affected part becomes a set dose before an X-ray irradiation time reaches 4 seconds, and thus there is a probability that irradiation with an X-ray on the affected part may be finished. In this case, the information indicating a cyclic change in a dose rate associated with body motion of a patient, illustrated in FIG. 13, cannot be created.

Therefore, in prior therapy planning, a range of a dose rate for performing respiration synchronized irradiation is determined. The range of a dose rate is a range between a dose rate d1 and a dose rate d2 illustrated in FIG. 13. The dose rates d1 and d2 are stored in the database 92. In a period T (refer to FIG. 13) in which motion of the affected part is gentle within the expiration period, the affected part is irradiated with an X-ray, and thus the affected part can be irradiated with an X-ray if the affected part is present at a substantially identical position even in a case where a position of the affected part is changed due to respiration. The dose rate d2 is a dose rate of a start point and an end point of the period T, and is a set dose rate. The dose rate d1 is the lowest dose rate in the period T.

Respiratory synchronization control of the present example is performed by the respiratory synchronization control device 25 as follows.

The respiratory synchronization control device 25 permits the X-ray 39 to be applied to the affected part of the patient 27 lying on the bed 15 for a very short time such as 10 msec. Thus, the electron beam generation portion 7 of the X-ray generation device 6 receives an irradiation permission command from the respiratory synchronization control device 25, and emits electrons for 10 msec. The X-ray 39 generated from the target 10 due to emission of the electrons is applied to the affected part of the patient 27 for 10 msec. The radiation detector 18 inserted into the body detects the X-ray 39. The dose calculation device 21 obtains a dose rate on the basis of an output signal from the radiation detector 18. The respiratory synchronization control device 25 performs control of the following (a), (b), (c), and (d).

(a) In a case where a dose rate which is input from the dose calculation device 21 due to X-ray irradiation for 10 msec is included in a range (d1 to d2) of a dose rate in an expiration period defined in a therapy plan, that is, the dose rate is equal to or lower than a set dose rate (dose rate d2) (second set dose rate) for respiratory synchronization control in the expiration period, the affected part is continuously irradiated with the X-ray 39, (b) in a case where a dose rate which is input from the dose calculation device 21 exceeds the set dose rate in the expiration period due to continuous irradiation with the X-ray 39, the respiratory synchronization control device 25 outputs an irradiation stop command to the electron beam generation portion 7 so as to stop irradiation with the X-ray 39 on the affected part, (c) in a case where a dose rate which is input from the dose calculation device 21 exceeds the set dose rate due to X-ray irradiation for 10 msec, the affected part is not irradiated with the X-ray 39 through control using an irradiation stop command after 10 msec elapses, and (d) the affected part is irradiated with the X-ray 39 for 10 msec in a case where, for example, 300 msec elapses after X-ray irradiation for 10 msec is finished. The period of 300 msec in which the affected part is not irradiated with an X-ray may be set to any length for the respiratory synchronization control device 25 by an operator. The second set dose rate (for example, the dose rate d2) is a set dose rate used for respiratory synchronization control which is control for irradiating the affected part of the patient 27 with radiation in synchronization with respiration of the patient 27.

The respiratory synchronization control device 25 performs the control of (d), and then performs the control of each of (a) and (b), or the control of (c). In the present example, the control of (d), and the control of each of (a) and (b) or the control of (c) according to a dose rate which is input from the dose calculation device 21 due to the control of (d) are repeatedly performed. As mentioned above, in the present example, it is possible to perform X-ray respiration synchronized irradiation in which, in a case where a dose rate obtained by the respiratory synchronization control device 25 on the basis of an output signal from the radiation detector 18 is equal to or lower than a set dose rate (the second set dose rate: for example, the dose rate d2), the affected part is irradiated with the X-ray 39, and, in a case where the obtained dose rate exceeds the set dose rate, the affected part is stopped being irradiated with the X-ray 39.

In the above-described present example, it is checked whether or not a dose rate is equal to or lower than a set dose rate through irradiation with an X-ray on the affected part, and thus irradiation with an X-ray on the affected part is required to exceed the set dose rate. However, an X-ray irradiation time is a very short time such as 10 msec, and can thus be restricted to below 1% with respect to about 1 sec which is a respiration cycle.

The timer provided in the dose calculation unit 24 (or the central control device 91) is activated in response to input of an irradiation permission command output from the respiratory synchronization control device 25, and is stopped in response to input of an irradiation stop command output from the respiratory synchronization control device 25. In a case where respiration synchronized irradiation is performed by the respiratory synchronization control device 25, a time period between input of the irradiation permission command and input of the irradiation stop command is measured every time. The dose calculation unit 24 calculates a dose applied to the affected part by using an obtained dose rate and a radiation irradiation time measured by the timer.

A description will be made of feedback control performed by the feedback control device 26. The feedback control device 26 performs feedback control on the basis of a dose (or a dose rate) obtained by the dose calculation unit 24 in respective processes in steps S3 to S5 illustrated in FIG. 7. In a case where it is determined that the dose $I_k$ obtained by the dose calculation unit 24 becomes the set dose (first set dose rate) $PI_k$ in step S4, the feedback control device 26 stops to irradiate the affected part with an X-ray (step S5).

In the present example, in addition to the effects of (1) to (3) achieved in Example 1, effects of (4) and (5) described below can be achieved.

(4) In the present example, respiratory synchronization control is performed in which the dose calculation unit 24 obtains a dose rate on the basis of an X-ray detected by the radiation detector 18, the X-ray 39 is applied to the affected part of the patient 27 which is a radiation irradiation target in a case where the dose rate is reduced to become the second set dose rate for respiratory synchronization control, the X-ray 39 is continuously applied to the affected part in a case where the dose rate is lower than the second set dose rate, and the X-ray 39 is stopped being applied to the affected part in a case where the dose rate exceeds the second set dose rate. Therefore, as described above, a dose rate with high accuracy can be obtained, and thus it is possible to perform respiration synchronized irradiation with an X-ray on the affected part with high accuracy by excluding the influence of body motion due to respiration. Thus, even if body motion occurs due to respiration, an X-ray can be intensively applied to the affected part, and thus it is possible to notably suppress X-ray irradiation on a healthy cell present in the vicinity of the affected part. Even in a case where a healthy cell highly sensitive to an X-ray is present in the vicinity of the affected part irradiated with the X-ray, it is possible to prevent the healthy cell from being damaged by the X-ray. Thus, an X-ray can be intensively applied to the affected part, and thus it is possible to widen a range in which X-ray therapy is applicable, that is, it is possible to increase the number of organs to which X-ray therapy is applicable.

(5) Since respiration synchronized irradiation with an X-ray on the affected part is performed through the above-described respiratory synchronization control using a dose rate which is obtained by the dose calculation unit 24 on the basis of an X-ray detected by the radiation detector 18, an ultrasonic tomographic apparatus and a probe a respiration monitor, an infrared light emitting diode and a semiconductor position detection element, or an LED or an LED light reflector and a camera, which detect body motion of the patient 27 and are used for respiratory synchronization control of the related art, are not necessary, and a structure of the X-ray therapy apparatus 1A can be simplified.

There may be a configuration in which a patient is put to sleep on a bed other than the bed 15, a cyclic change in body motion of the patient is measured in advance by a well-known respiration monitor in a stable state, and information indicating the cyclic change in body motion corresponding to a respiration cycle may be created on the basis of a measurement result. In a case where information indicating a cyclic change in body motion corresponding to a respiration cycle is created by using a measured value in the respiration monitor, a cycle of the period T can be understood on the basis of the information.

In a case where information regarding the cycle of the period T is used, the X-ray irradiation for 10 msec can be matched with a start point of the period T with high efficiency, and thus it is possible to increase a period of respiration synchronized irradiation. In other words, an output time point of the next irradiation stop command from an output point (an end point of the period T) of an irradiation stop command from the respiratory synchronization control device 25 in the above (b) is obtained by using the information regarding the cycle of the period T, and an "output point of the next irradiation permission command" corresponding to the "output point of the next irradiation stop command" is obtained by subtracting the period T from the obtained "output point of the next irradiation stop command". A time (time point) for the "output point of the next irradiation permission command" is obtained by the respiratory synchronization control device 25. The respiratory synchronization control device 25 outputs an irradiation permission command to the electron beam generation portion 7 at the obtained time. The respiratory synchronization control device 25, which receives a dose rate obtained by the dose calculation unit 24 on the basis of a signal output from the radiation detector 18 detecting the X-ray 39 applied to the affected part, determines whether or not the dose rate is equal to or lower than a set dose rate. The obtained time is substantially a start time of the period T, and thus the affected part is continuously irradiated with the X-ray 39 through respiration synchronized irradiation during the period T. In a case where the dose rate obtained by the dose calculation unit 24 exceeds the set dose rate (in a case where the period T ends), an irradiation stop command is output from the respiratory synchronization control device 25, and thus the affected part is stopped being irradiated with the X-ray 39. The respiratory synchronization control device 25 can obtain a time at which the subsequent irradiation permission command is output by using the time for the "output point of the next irradiation permission command" and the information regarding the cycle of the period T, can output an irradiation permission command when the time comes, and can perform respiration synchronized irradiation while checking that the obtained dose rate is equal to or lower than the set dose rate.

In a case where pre-radiation irradiation illustrated in FIG. 11 is performed, in pre-radiation irradiation of applying an X-ray having a low X-ray intensity to the affected part, information indicating a cyclic change in a dose rate associated with body motion of the patient illustrated in FIG. 13 may be created by using the dose rate which is obtained by the dose calculation unit 24 on the basis of a signal output from the radiation detector 18 inserted into the body for 4 or 5 seconds after the affected part is irradiated with an X-ray. This information is registered in a memory (not illustrated) of the respiratory synchronization control device 25.

Hereinafter, a description will be made of X-ray respiration synchronized irradiation based on information indicating a cyclic change in a dose rate associated with body motion of a patient, illustrated in FIG. 13.

The respiratory synchronization control device 25 outputs an activation control command to the electron beam generation portion 7 at a start point of the period T (refer to FIG. 13) at which motion of the affected part is gentle within the expiration period, that is, at a time point at which a dose rate obtained by the dose calculation unit 24 is reduced to become a set dose rate (dose rate d2) (second set dose rate), on the basis of the information indicating the cyclic change in the dose rate associated with body motion of the patient, registered in a memory. The respiratory synchronization control device 25 outputs a stop control command at an end point of the period T, that is, at a time point at which the obtained dose rate exceeds the set dose rate. The X-ray 39 generated from the target 10 is applied to the affected part of the patient 27 on the bed 15 in the period T (the period T until the dose rate obtained by the dose calculation unit 24 is reduced to the set dose rate in the expiration period, and is then increased to the set dose rate again (the period in which the obtained dose rate is equal to or lower than the set dose rate)) until a stop control command is output after an activation control command is output to the electron beam generation portion 7.

A cycle of the period T may be obtained by the respiratory synchronization control device 25 on the basis of the information indicating a cyclic change in the dose rate associated with body motion of the patient, illustrated in FIG. 13. The respiratory synchronization control device 25 outputs an activation control command and a stop control command to the electron beam generation portion 7 on the basis of the obtained dose rate corresponding to the cycle of the period T. As a result, the affected part can be irradiated with an X-ray in each cyclic period T in which motion of the affected part is gentle in body motion due to respiration. As mentioned above, the X-ray therapy apparatus 1A can perform respiration synchronized irradiation with an X-ray on the affected part even by using the information indicating a cyclic change in the dose rate associated with body motion of the patient, illustrated in FIG. 13, created by using the dose rate obtained in the pre-radiation irradiation. However, since the intensity of an X-ray applied to the affected part is low in the pre-radiation irradiation, the information indicating a cyclic change in the dose rate associated with body motion of the patient, created on the basis of the dose rate in the pre-radiation irradiation is required to be corrected by taking into consideration the intensity of an applied X-ray in main radiation irradiation. Thus, a corrected value is used as a set dose rate used for respiration synchronized irradiation.

The respiratory synchronization control device 25 monitors the dose rate obtained by the dose calculation unit 24 in each period T. In a case where the dose rate obtained in the period T is more than an average value (set dose rate) of dose rates in the respective periods T, obtained on the basis of detection signals of X-rays detected by the radiation detector 18 in order to create the information indicating the cyclic change in the dose rate associated with body motion of the patient, the respiratory synchronization control device 25 regards a cycle of the period T to be deviated or the dose rate to be increased due to disruption of respiration, and outputs a stop control command to the electron beam generation portion 7 such that the affected part is stopped being irradiated with an X-ray. Thus, it is possible to reduce irradiation with an X-ray on healthy cell tissue due to respiration synchronized irradiation.

The feedback control device 26 may control the respective processes in steps S6, S4, and S5 illustrated in FIG. 9, or the respective processes in steps S7, S8, S4, and S5 illustrated in FIG. 10, instead of the respective processes in steps S3, S4, and S5 illustrated in FIG. 7. The feedback control device 26 may control respective processes in steps S9 to S12, S4, and S5 illustrated in FIG. 11 instead of the respective processes in steps S3, S4, and S5 illustrated in FIG. 7.

The respective processes in steps S9 and S11 are performed by the central control device 91, step S10 is performed by the dose calculation device 21, and steps S12, S4, and S5 are performed by the feedback control device 26.

Example 3

Figure 14:
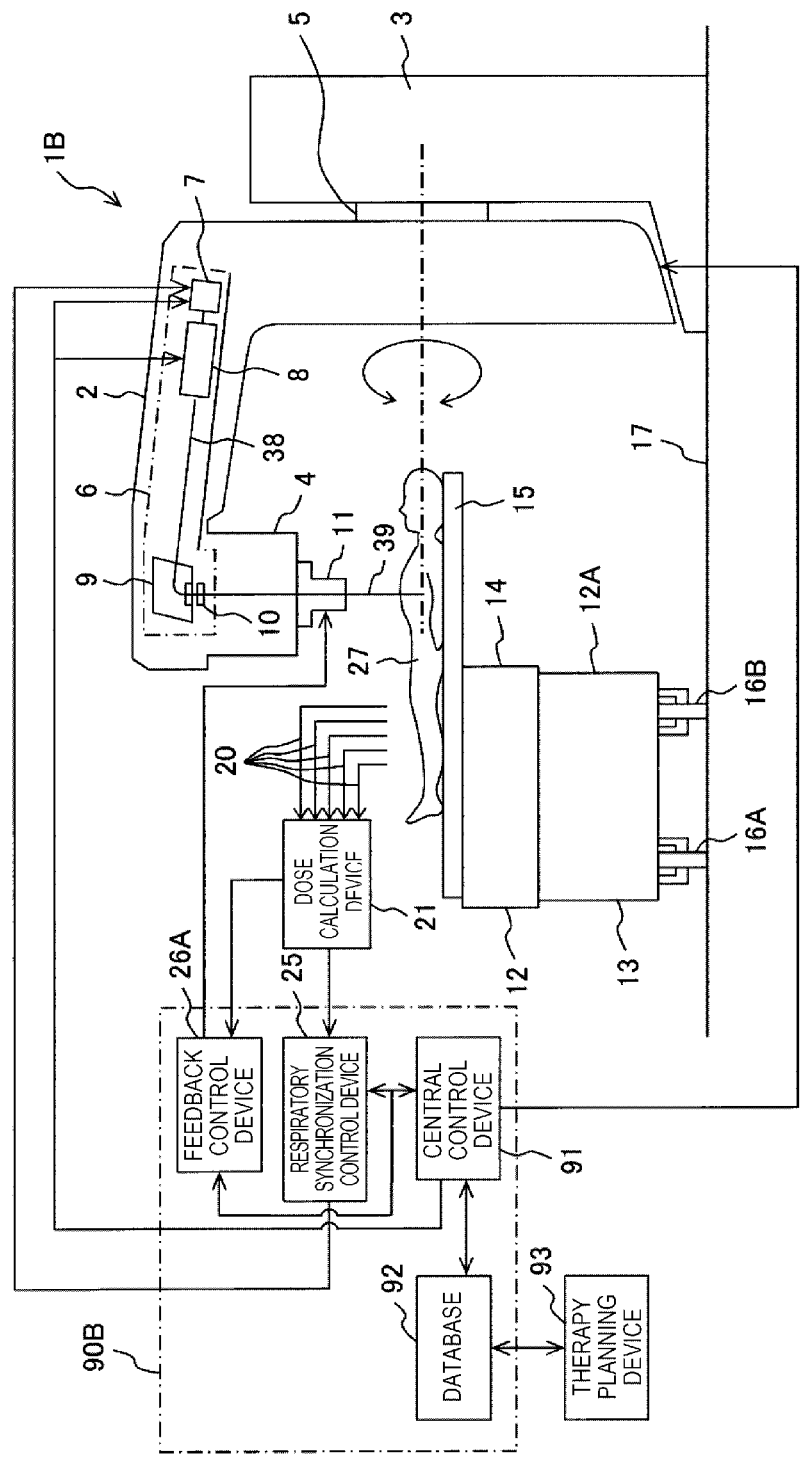
FIG. 14 is a configuration diagram of an X-ray therapy apparatus which is a radiation therapy apparatus of Example 3 which is still another preferable example of the present invention.

A description will be made of a radiation therapy apparatus of Example 3 which is still another preferable example of the present invention with reference to FIG. 14. The radiation therapy apparatus of the present example is an X-ray therapy apparatus. An X-ray therapy apparatus 1B of the present example has a configuration in which the control system 90A is replaced with a control system 90B in the X-ray therapy apparatus 1A of Example 2. Other configurations of the X-ray therapy apparatus 1B are the same as those of the X-ray therapy apparatus 1A. The control system 90B has a configuration in which the feedback control device 26 is replaced with a feedback control device (first control device) 26A in the control system 90A. Other configurations of the control system 90B are the same as those of the control system 90A. A control target of the feedback control device 26A is the variable collimator 11 unlike a control target of the feedback control device 26 of the X-ray therapy apparatus 1.

In X-ray therapy using the X-ray therapy apparatus 1B, a plurality of radiation detectors 18 are also inserted into the body of the patient 27 on the bed 15. A cancer therapy method using the X-ray therapy apparatus 1B is the same as the cancer therapy method using the X-ray therapy apparatus 1A of Example 2 except that the variable collimator 11 is controlled by the feedback control device 26A. Thus, herein, a description will be made of control of the variable collimator 11 performed by the feedback control device 26A.

The feedback control device 26A performs feedback control on the basis of the dose rate obtained by the dose calculation unit 24 in the respective processes in steps S3 to S5 illustrated in FIG. 7. In step S3, in a case where the obtained dose $I_k$ does not become the set dose $PI_k$ defined in the therapy plan, an opening shape of the variable collimator 11 (irradiation condition) is adjusted such that a dose distribution in the affected part becomes a dose distribution defined in the therapy plan, that is, the dose $I_k$ (where k is an integer of 1 to N) becomes the set dose $PI_k$ (where k is an integer of 1 to N) defined in the therapy plan, through control performed by the feedback control device 26A.

The present example can achieve the respective effects of (1) to (5) achieved in Example 2. In the present example, in a case where the dose $I_k$ (where k is an integer of 1 to N) does not become the set dose $PI_k$ (where k is an integer of 1 to N), an opening shape of the variable collimator 11 is controlled, and thus it is possible to obtain an appropriate dose distribution by irradiating the affected part with an X-ray.

In a case where the control performed by the feedback control device 26 illustrated in FIG. 11 is applied to the present example, an irradiation condition determined in step S12 illustrated in FIG. 11 is an opening shape of the variable collimator 11.

Example 4

Figure 15:
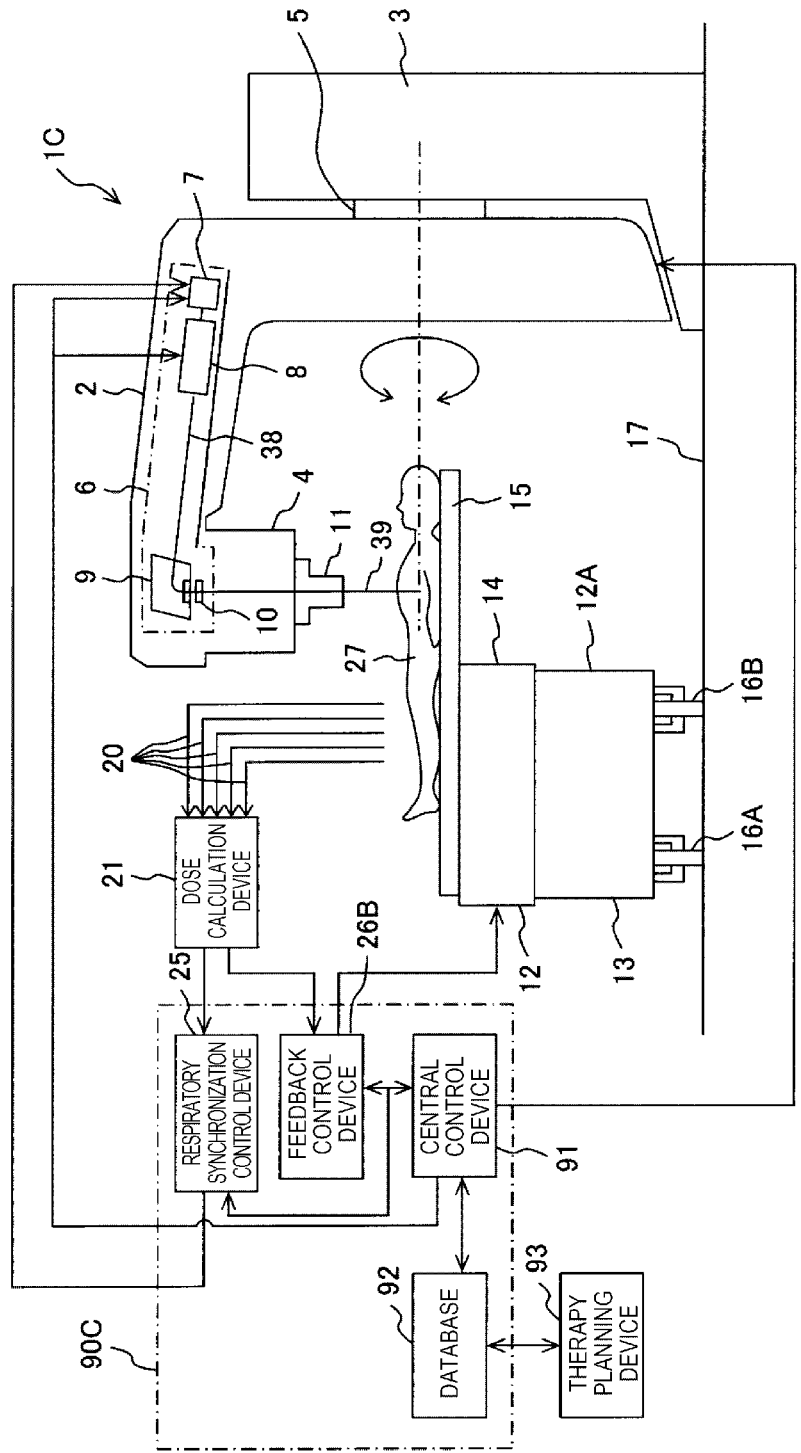
FIG. 15 is a configuration diagram of an X-ray therapy apparatus which is a radiation therapy apparatus of Example 4 which is still another preferable example of the present invention.

A description will be made of a radiation therapy apparatus of Example 4 which is still another preferable example of the present invention with reference to FIG. 15.

The radiation therapy apparatus of the present example is an X-ray therapy apparatus. An X-ray therapy apparatus 1C of the present example has a configuration in which the control system 90A is replaced with a control system 90C in the X-ray therapy apparatus 1 of Example 2. Other configurations of the X-ray therapy apparatus 1C are the same as those of the X-ray therapy apparatus 1A. The control system 90C has a configuration in which the feedback control device 26 is replaced with a feedback control device (first control device) 26B in the control system 90A. Other configurations of the control system 90C are the same as those of the control system 90A. A control target of the feedback control device 26B is a position of the bed 15 unlike a control target of the feedback control device 26 of the X-ray therapy apparatus 1.

In X-ray therapy using the X-ray therapy apparatus 1C, a plurality of radiation detectors 18 are also inserted into the body of the patient 27 on the bed 15. A cancer therapy method using the X-ray therapy apparatus 1C is the same as the cancer therapy method using the X-ray therapy apparatus 1A of Example 2 except that a position of the bed 15 is controlled by the feedback control device 26B. Thus, herein, a description will be made of control of a position of the bed 15 performed by the feedback control device 26B.

The feedback control device 26B performs feedback control on the basis of the dose rate obtained by the dose calculation unit 24 in the respective processes in steps S3 to S5 illustrated in FIG. 7. In step S3, in a case where the obtained dose $I_k$ does not become the set dose $PI_k$ defined in the therapy plan, a position of the bed 15 (irradiation condition) is adjusted such that a dose distribution in the affected part becomes a dose distribution defined in the therapy plan, that is, the dose $I_k$ (where k is an integer of 1 to N) becomes the set dose $PI_k$ (where k is an integer of 1 to N) defined in the therapy plan, through control performed by the feedback control device 26B.

The present example can achieve the respective effects of (1) to (5) achieved in Example 2. In the present example, in a case where the dose $I_k$ (where k is an integer of 1 to N) does not become the set dose $PI_k$ (where k is an integer of 1 to N), a position of the bed 15 is controlled, and thus it is possible to obtain an appropriate dose distribution by irradiating the affected part with an X-ray.

In a case where the control performed by the feedback control device 26 illustrated in FIG. 11 is applied to the present example, an irradiation condition determined in step S12 illustrated in FIG. 11 is a position of the bed 15.

Example 5

A description will be made of a radiation therapy apparatus of Example 5 which is still another preferable example of the present invention with reference to FIG. 16. The radiation therapy apparatus of the present example is a particle beam therapy apparatus.

A particle beam therapy apparatus 41 of the present example includes a dose calculation device 21, an ion beam generation device 42, a high energy beam transport system (HEBT system) 54, a gantry beam transport system (GABT system) 61, a rotation gantry 56, an irradiation device 69, and a control system 73. In the particle beam therapy apparatus 41, a proton ion beam is used as an ion beam applied to an affected part (beam irradiation target) of cancer. A carbon ion beam may be used instead of a proton ion beam.

The ion beam generation device (radiation generation device) 42 includes an ion source (not illustrated), a linear accelerator 45 which is a pre-accelerator, and a synchrotron accelerator 43. The synchrotron accelerator 43 includes an annular beam duct 44 configuring a circulating track of an ion beam, an injector 45A, a high frequency acceleration cavity (high frequency acceleration device) 48 which applies a high frequency voltage to an ion beam, a plurality of deflection electromagnets 46, a plurality of quadrupole electromagnets 47, a high frequency applying device 49 for emission and a septum electromagnet 53 for emission. The injector 45A connected to the beam duct 44 is connected to the linear accelerator 45 via a vacuum duct. The ion source is also connected to the linear accelerator 45. The high frequency applying device 49 includes an emission high frequency electrode 50, a high frequency power source 51, and a switch 52. The emission high frequency electrode 50 is attached to the annular beam duct 44, and is connected to the high frequency power source 51 via the switch 52. The respective deflection electromagnets 46, the respective quadrupole electromagnets 47, the high frequency acceleration cavity 48, and the septum electromagnet 53 are disposed along the beam duct 44 as illustrated in FIG. 16.

The HEBT system (first beam transport system) 54 has a beam path (beam duct) 55 connected to the septum electromagnet 53 of the synchrotron accelerator 43, and is configured to include a shutter 58, a deflection electromagnet 57, and a plurality of quadrupole electromagnets 59 disposed long the beam path 55 from the synchrotron accelerator 43 toward the irradiation device 69.

The GABT system (second beam transport system) 61 has a beam path (beam duct) 62, and is configured to include a deflection electromagnet 63, quadrupole electromagnets 67 and 68, and deflection electromagnets 64 and 65 disposed long the beam path 62 from the synchrotron accelerator 43 toward the irradiation device 69. The beam path 62 and the respective electromagnets of the GABT system 61 are attached to the rotation gantry 56. The beam path 62 is connected to the beam path 55 at a connection portion 60 between the HEBT system 54 and the GABT system 61. The beam path 62 is rotated by the rotation gantry 56. Thus, the beam path 62 is not directly connected to the beam path 55.

The irradiation device 69 includes two scanning electromagnets (ion beam scanning devices) 70 and 71, and a beam position monitor 72. The irradiation device 69 is attached to the rotation gantry 56, and is disposed on the downstream side of the deflection electromagnet 65. The scanning electromagnets 70 and 71 and the beam position monitor 72 are disposed in this order along a central line of the irradiation device 69 from the deflection electromagnet 65 toward an ion beam outlet of the irradiation device 69 in the irradiation device 69. The scanning electromagnet 70 deflects an ion beam in a plane perpendicular to the central line of the irradiation device 69, so as to perform scanning with the ion beam in the X direction, and the scanning electromagnet 71 deflects an ion beam in the plane so as to perform scanning with the ion beam in the Y direction orthogonal the X direction. The bed 15 on which the patient 27 lies is disposed to face a front end of the irradiation device 69.

Figure 16:
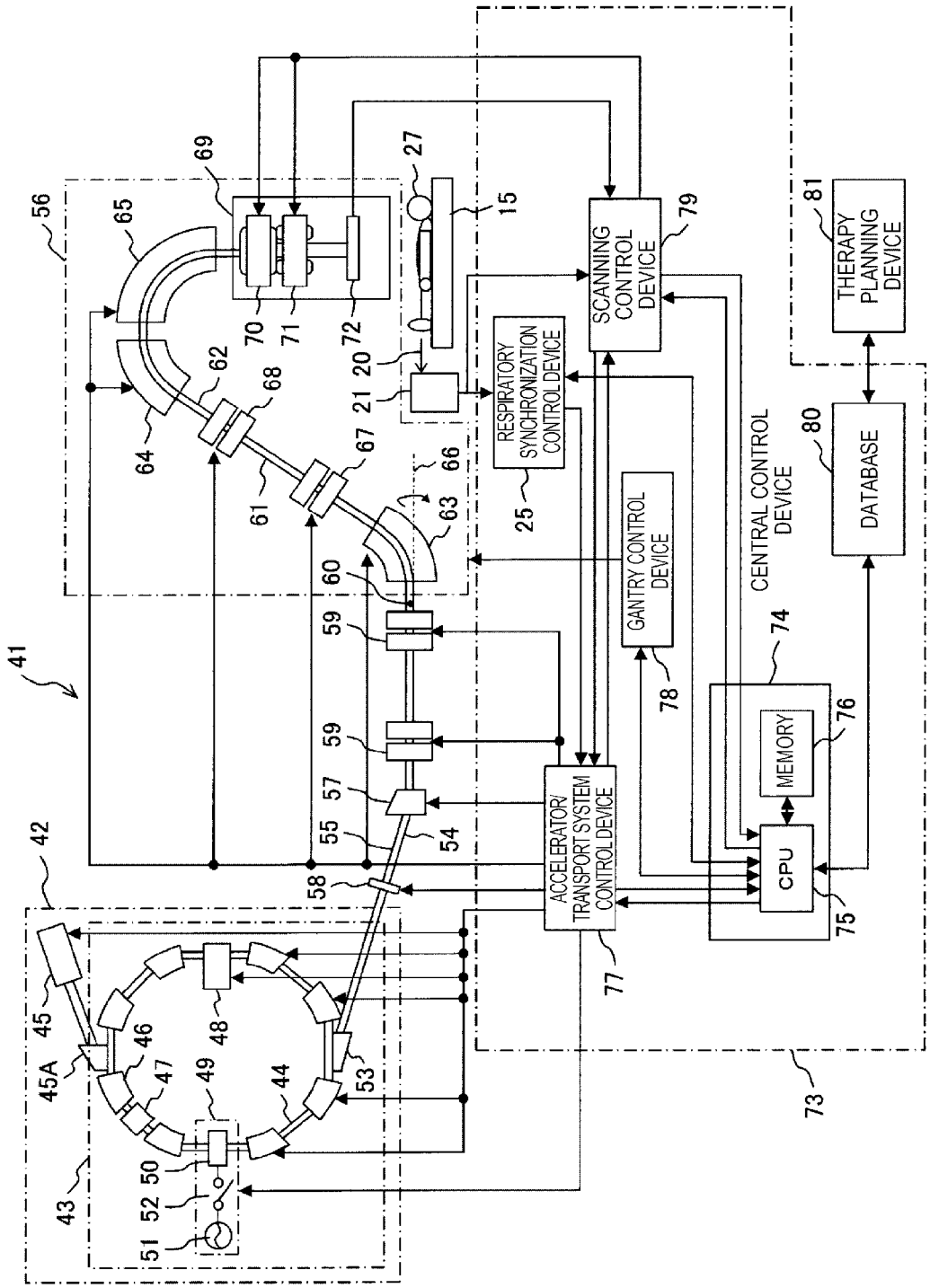
FIG. 16 is a configuration diagram of a particle beam therapy apparatus which is a radiation therapy apparatus of Example 5 which is still another preferable example of the present invention.

The control system 73 includes a respiratory synchronization control device 25, a central control device 74, an accelerator/transport system control device 77, a gantry control device 78, a scanning control device 79, and a database 80 (refer to FIG. 16). The central control device 74 has a central processing unit (CPU) 75 and a memory 76 connected to the CPU 75. The CPU 75 is connected to the respiratory synchronization control device 25, the accelerator/transport system control device 77, the scanning control device 79, and the gantry control device 78. The database 80 is connected to the CPU 75. The particle beam therapy apparatus 41 includes a therapy planning device 81, and the therapy planning device 81 is connected to the database 80.

Although not illustrated, the rotation gantry 56 is supported by a pair of support devices fixed to a floor of a treatment room in which the particle beam therapy apparatus 41 is installed. Each of the support devices includes a plurality of rotatable support rollers. The rotation gantry 56 is supported by the plurality of support rollers of each of the support devices. A rotation device (for example, a motor) rotating the rotation gantry 56 is connected to one support roller among the plurality of support rollers of one of the pair of support devices.

The beam path 62 of the GABT system 61 is connected to the beam path 55 of the HEBT system 54 at the connection portion 60 located outside the rotation gantry 56. A central line 66 (refer to FIG. 16) of the rotation gantry 56 is the rotation center of the rotation gantry 56, and passes through the center of an inlet of the beam path 62 at the connection portion 60.

The bed 15 is attached to drive mechanisms although not illustrated. The drive mechanisms includes, although not illustrated, an X direction drive mechanism, a Y direction drive mechanism, a vertical direction drive mechanism, and a rotation drive mechanism. The drive mechanisms are disposed outside the rotation gantry 56. The vertical direction drive mechanism is installed on the X direction drive mechanism, the Y direction drive mechanism is provided on the vertical direction drive mechanism, and the rotation drive mechanism is provided on the Y direction drive mechanism. The bed 15 is installed on the rotation drive mechanism, and is supported by each drive mechanism.

Figure 2:
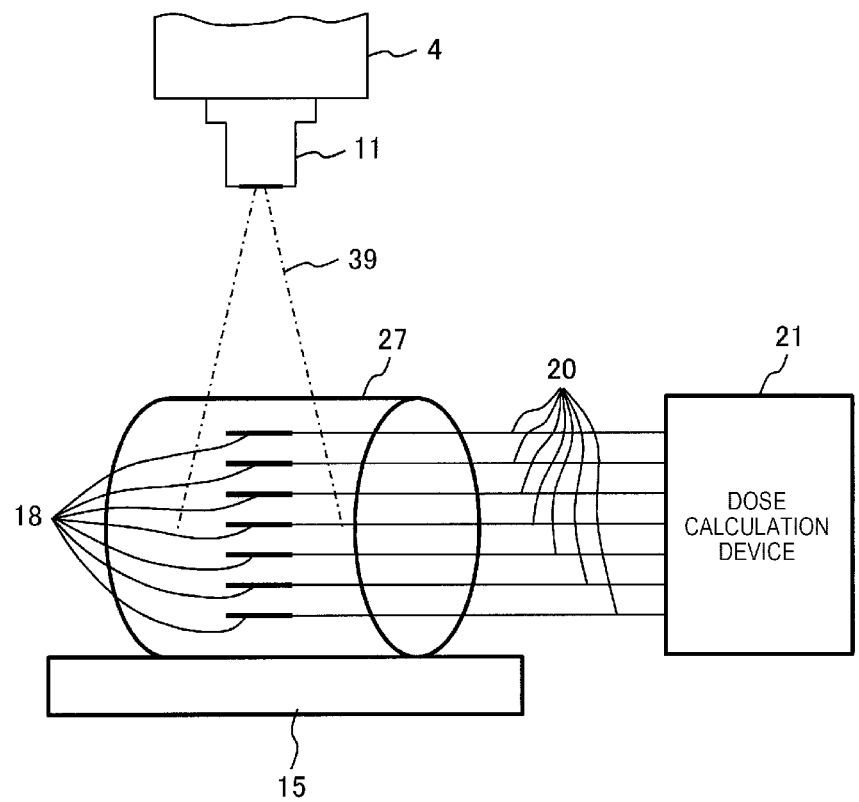
FIG. 2 is a schematic diagram illustrating a radiation detector inserted into the body of a patient on a bed illustrated in FIG. 1.

As illustrated in FIG. 2, a plurality of radiation detectors 18 are inserted into the body of the patient 27 on the bed 15.

As illustrated in FIG. 5, the dose calculation device 21 includes a photoelectric converter 22, a counting unit 23, and a dose calculation unit 24. The optical fiber 20 connected to each of the plurality of radiation detectors 18 inserted into the body of the patient 27 is connected to the photoelectric converter 22 of the dose calculation device 21.

A description will be made of cancer therapy of the patient using the particle beam therapy apparatus 41.

Prior to cancer therapy using irradiation with a proton ion beam, therapy planning for the affected part of the patient 27 subjected to the therapy is performed by using the therapy planning device 81. In this therapy planning, an irradiation direction of a proton ion beam (hereinafter, simply referred to as an ion beam) on the affected part, a plurality of separate layers $L_i$ (where i=1, 2, ..., and m) included in the affected part in this irradiation direction (a depth direction from a body surface of the patient), a central position (target position) $P_{i,j}$ of a plurality of irradiation spots $A_{i,j}$ (where i=1, 2, ..., and m, and j=1, 2, ..., and n) which are irradiation regions in each layer, an order of irradiation with an ion beam on the irradiation spots $A_{i,j}$, and a target dose $R0_{i,j}$ for each of the irradiation spots $A_{i,j}$, are determined. Therapy plan information such as energy $E_i$ of an ion beam corresponding to each layer $L_i$ is registered in the database 80 (refer to paragraphs [0050] and [0051] in JP-A-2015-157003).

The affected part subjected to therapy is divided into a plurality of layers, that is, layers $L_1$, $L_2$, $L_3$, ..., and $L_m$ (refer to FIG. 5 in JP-A-2015-157003). The layer $L_1$ is present at the deepest position from the body surface, the depth of the layers is reduced in an order of the layers $L_2$, $L_3$, ..., and $L_m$, and the layer Lm is present at the shallowest position. An ion beam is applied in a direction of an arrow 50 as illustrated in FIG. 5.

The patient 27 subjected to the therapy is placed on the bed 15. Before the affected part of the patient 27 is irradiated with an ion beam, the bed 15 is positioned, and the central line of the irradiation device 69 is positioned in the ion beam irradiation direction. The bed 15 is positioned such that the affected part is located on the central line of the irradiation device 69 by driving the X direction drive mechanism, the Y direction drive mechanism, the vertical direction drive mechanism, and the rotation drive mechanism. The positioning of the central line of the irradiation device 69 in the ion beam irradiation direction is performed by the gantry control device 78 rotating the rotation gantry 56 by a predetermined angle such that the central line of the irradiation device 69 is aligned with the ion beam irradiation direction defined in the therapy plan.

In the cancer therapy of the patient of the present example, among the respective processes in steps S1 to S19 disclosed in JP-A-2015-157003, all remaining steps except for steps S6, S12, S13, S18, and S19 are performed. Among steps S1 to S5, S7 to S9, S9A, S10, S11, and S14 to S17, the respective processes in steps S1 to S3 and S5 are performed by the accelerator/transport system control device 77, and steps S4, S7 to S9, S9A, S11, and S14 to S17 are performed by the scanning control device 79. As disclosed in JP-A-2015-157003, among the respective processes S4, S7 to S9, S10, S9A, S11, and S14 to S17 performed by the scanning control device 79, the respective processes in steps S4, S10, S11, and S14 to S17 are performed by an irradiation position control device (not illustrated), the respective processes in steps S7 to S9, and S9A are performed by a dose determination device (not illustrated), and the respective processes in steps S11 to S13, and S16 are performed by a layer determination device (not illustrated). The scanning control device 79 includes the irradiation position control device, the dose determination device, and the layer determination device. The reference signs S1 to S5, S7 to S9, S9A, S10, S11, and S14 to S17 indicating steps used in the present example and Example 6 which will be described later indicate corresponding steps disclosed in JP-A-2015-157003 unlike S1 to S12 illustrated in FIGS. 7, and 9 to 11 described in Example 2.

The respective processes in step S1 (control of each electromagnet of the beam transport system), step S2 (activation of the linear accelerator 45), step S3 (acceleration of an ion beam in the synchrotron accelerator 43), step S4 (setting of an irradiation position of an ion beam at a target position P of an irradiation spot), step S5 (emission of an ion beam from the synchrotron accelerator 43), and step S7 (a determination of whether or not a dose $R_{i,j}$ in the irradiation spots $A_{i,j}$ becomes the target dose $R0_{i,j}$) are sequentially performed as disclosed in JP-A-2015-157003. The shutter 58 is opened by the accelerator/transport system control device 77 in step S1.

In step S4, the irradiation position control device included in the scanning control device 79 controls excitation currents respectively supplied to the scanning electromagnets 70 and 71 so as to adjust deflection electromagnetic forces respectively generated in the scanning electromagnets 70 and 71 such that an ion beam reaches the irradiation spot $A_{i,j}$ in the layer $L_i$, for example, the initial irradiation spot $A_{1,1}$ in the layer $L_1$ located at the deepest position from the body surface. The irradiation position control device outputs a beam irradiation starting signal in a case where it is determined that the excitation currents respectively supplied to the scanning electromagnets 70 and 71 are controlled such that an ion beam reaches the irradiation spot $A_{i,j}$.

In step S5, a high frequency from the high frequency power source 51 is applied to an ion beam circulating inside the beam duct 44 from the emission high frequency electrode 50 under the control of the accelerator/transport system control device 77 receiving the beam irradiation starting signal. As a result, the circulating ion beam is emitted to the beam path 55 of the HEBT system 54 from the synchrotron accelerator 43 through the septum electromagnet 53. The ion beam is applied to the affected part of the patient 27 on the bed 15 from the irradiation device 69. Specifically, the ion beam is applied to the target position $P_{i,j}$ of the irradiation spot $A_{i,j}$ in the layer $L_i$ of the affected part.

The radiation detector 18 inserted into the body of the patient 27 detects the ion beam (an aggregate of proton beams) applied to the irradiation spot $A_{i,j}$ in the layer $L_i$. The light emitting portion 19 of the radiation detector 18 outputs a plurality of photons corresponding to total energy of a plurality of proton beams which are incident at one time, one by one with the time delay. The photons are converted into electric pulses by the photoelectric converter 22, the counting unit 23 counts the electric pulses so as to obtain a counting rate of the electric pulses, and the dose calculation unit 24 converts the counting rate of the electric pulses into a dose rate by using the information of the data table (characteristics in FIG. 6). The dose calculation unit 24 obtains a dose by using the dose rate.

After the ion beam irradiation is started, the respiratory synchronization control device 25 creates the information indicating the cyclic change in the dose rate associated with body motion of the patient, illustrated in FIG. 13, by using the dose rate obtained by the dose calculation unit 24 for 4 or 5 seconds, for example. This information is registered in a memory (not illustrated) of the respiratory synchronization control device 25.

As disclosed in JP-A-2015-157003, in a case where a determination result in step S7 is "No", the process in step S8 (continuation of irradiation with an ion beam) is performed, and the process in step S9 (a determination of whether or not the dose $R_{i,j}$ in the irradiation spot $A_{i,j}$ becomes the target dose $R0_{i,j}$) is also performed. In a case where a determination result in step S9 is "No", the processes in steps S8 and S9 are repeatedly performed until a determination result in step S9 is "Yes".

In a case where a determination result in step S9 is "Yes", the respective processes in steps S9A (output of a beam irradiation stopping signal) and S10 (stopping of irradiation with an ion beam on the irradiation spot $A_{i,j}$) are performed (refer to JP-A-2015-157003).

Next, the process in step S11 (a determination of whether or not irradiation on the layer $L_i$ is finished) is performed, and, in a case where a determination result in step S11 is "No", the processes in steps S14 (execution of j=j+1) and S15 (a determination of whether or not a circulating ion beam can be used) are performed as disclosed in JP-A-2015-157003. In a case where a determination result in step S15 is "Yes", the respective processes in steps S4, S5, S7 to S9, S9A, S10, and S11 are performed. In a case where a determination result in step S15 is "No", the respective processes in steps S2 to S5, S7 to S9, S9A, S10, and S11 are performed.

As disclosed in JP-A-2015-157003, in a case where a determination result in step S11 is "Yes", step S16 (a determination of whether or not irradiation with an ion beam on the target positions $P_{i,j}$ of all the irradiation spots $A_{i,j}$ in all the layers of the affected part is finished) is performed. In a case where a determination result in step S16 is "No", step S17 (execution of i=i+1) is performed, and, then, with respect to all the remaining layers $L_i$ present at shallow positions, the respective processes in steps S2 to S5, S7 to S9, S9A, S10, and S11 are repeatedly performed until a determination result in step S16 is "Yes", the respective processes in steps S14, S15, S2 to S5, S7 to S9, S9A, S10, and S11 (or the respective processes in steps S14, S15, S4, S5, S7 to S9, S9A, S10, and S11) are repeatedly performed until a determination result in step S11 is "Yes", and the respective processes in steps S16 and S17 are performed in a case where a determination result in step S11 is "Yes".

Also in the present example, in the same manner as in Example 2, the control of (a), (b), (c), and (d) is performed by the respiratory synchronization control device 25, the control of (d) is performed, and then the control of each of (a) and (b) or the control of (c) is performed, so that respiration synchronized irradiation is performed. The respiration synchronized irradiation is performed when an ion beam is applied to the irradiation spot $A_{i,j}$ in the layer $L_i$. In the respiration synchronized irradiation performed by the respiratory synchronization control device 25, in a case where the dose calculation unit 24 obtains a dose rate on the basis of a signal output from the radiation detector 18 in the body due to irradiation with an ion beam on the irradiation spot $A_{i,j}$ for 10 msec, and the dose rate is equal to or lower than a set dose rate (second set dose rate), an ion beam is applied to the irradiation spot $A_{i,j}$ until the dose rate exceeds the set dose rate, and an ion beam is stopped being applied to the irradiation spot $A_{i,j}$ in a case where the dose rate exceeds the set dose rate. In a case where the dose rate exceeds the set dose rate, the respiratory synchronization control device 25 outputs a stop control command to the accelerator/transport system control device 77 in order to stop irradiation with an ion beam on the irradiation spot $A_{i,j}$. In a case where irradiation with an ion beam on the irradiation spot $A_{i,j}$ is started, the respiratory synchronization control device 25 outputs an activation control command to the accelerator/transport system control device 77. The accelerator/transport system control device 77 turns on and off the switch 52 of the high frequency applying device 49 on the basis of the input activation control command and stop control command. The switch 52 is repeatedly turned on and off, and thus irradiation with an ion beam on the irradiation spot $A_{i,j}$ is repeatedly performed and stopped. Thus, respiration synchronized irradiation with an ion beam is performed on a single irradiation spot $A_{i,j}$. The activation control command in the present example corresponds to the irradiation permission command in Example 2, and the stop control command in the present example corresponds to the irradiation stop command in Example 2.

The respiration synchronized irradiation (described in Example 2) using information indicating a cyclic change of body motion corresponding to a cycle of respiration created in advance by using a measured value in the respiration monitor, or the respiration synchronized irradiation (described in Example 2) using information indicating a cyclic change in a dose rate associated with body motion of a patient, illustrated in FIG. 13, created by using a dose rate obtained by the dose calculation unit 24, may be performed instead of the above-described "respiration synchronized irradiation in which the control of (a), (b), (c), and (d) is performed, the control of (d) is performed, and then the control of each of (a) and (b) or the control of (c) is performed".

Also in the present example, the timer provided in the dose calculation unit 24 (or the central control device 91) is activated in response to input of an activation control command, and is stopped in response to input of a stop control command. In a case where respiration synchronized irradiation is performed, a time period between input of the activation control command and input of the stop control command is measured every time. The dose calculation unit 24 calculates a dose applied to the irradiation spot $A_{i,j}$ by using an obtained dose rate and a radiation irradiation time measured by the timer.

In step S9, the dose determination device of the scanning control device 79 receives the dose obtained by the dose calculation unit 24, and determines whether or not the dose $R_{i,j}$ in the irradiation spot $A_{i,j}$ becomes the target dose $R0_{i,j}$ on the basis of the dose. In a case where a determination result in step S9 is "No", the respective processes in steps S8 and S9 are repeatedly performed until the dose $R_{i,j}$ in the irradiation spot $A_{i,j}$ becomes the target dose $R0_{i,j}$. In a case where a determination result in step S9 is "Yes", the dose determination device outputs a beam irradiation stopping signal in step S9A. In a case where the dose $R_{i,j}$ in the irradiation spot $A_{i,j}$ becomes the target dose $R0_{i,j}$, the dose determination device outputs a beam irradiation stopping signal to the irradiation position control device. The irradiation position control device outputs the beam irradiation stopping signal to the accelerator/transport system control device 77, and the accelerator/transport system control device 77 having received the stopping signal opens the switch 52. A high frequency is stopped being applied to the emission high frequency electrode 50, an ion beam is stopped being emitted from the synchrotron accelerator 43, and the irradiation spot $A_{i,j}$ of the affected part is stopped being irradiated with an ion beam.

Thereafter, since a determination result in step S11 is "No", the respiratory synchronization control device 25 sequentially performs the respiration synchronized irradiation with an ion beam on all the remaining irradiation spots $A_{i,j}$ in the layer $L_j$.

In a case where a determination result in step S16 is "No", respiration synchronized irradiation with an ion beam is sequentially performed on all the irradiation spots $A_{i,j}$ in each of the remaining layers $L_j$. Irradiation with an ion beam on the remaining layers $L_j$ is performed by the accelerator/transport system control device 77 controlling a high frequency voltage applied to the ion beam circulating inside the beam duct 44 from the high frequency acceleration cavity 48 such that energy of the ion beam is adjusted in step S3. As the energy of the ion beam is reduced, the ion beam is applied to the shallow layer $L_j$ from the body surface. Irradiation with an ion beam on all the irradiation spots $A_{i,j}$ in the remaining layers $L_j$ is also performed through respiration synchronized irradiation in the respiratory synchronization control device 25.

In a case where respiration synchronized irradiation on all the irradiation spots $A_{i,j}$ in all the layers $L_j$ is finished, that is, a determination result in step S16 is "Yes", irradiation with an ion beam on the affected part is finished.

In the same manner as in Example 2, in the present example, multiple-field irradiation in which an affected part is irradiated with an ion beam from a plurality of ion beam irradiation directions may be performed.

The present example can achieve the effects of (1) to (4) among the effects achieved in Example 2.

Example 6

Figure 17:
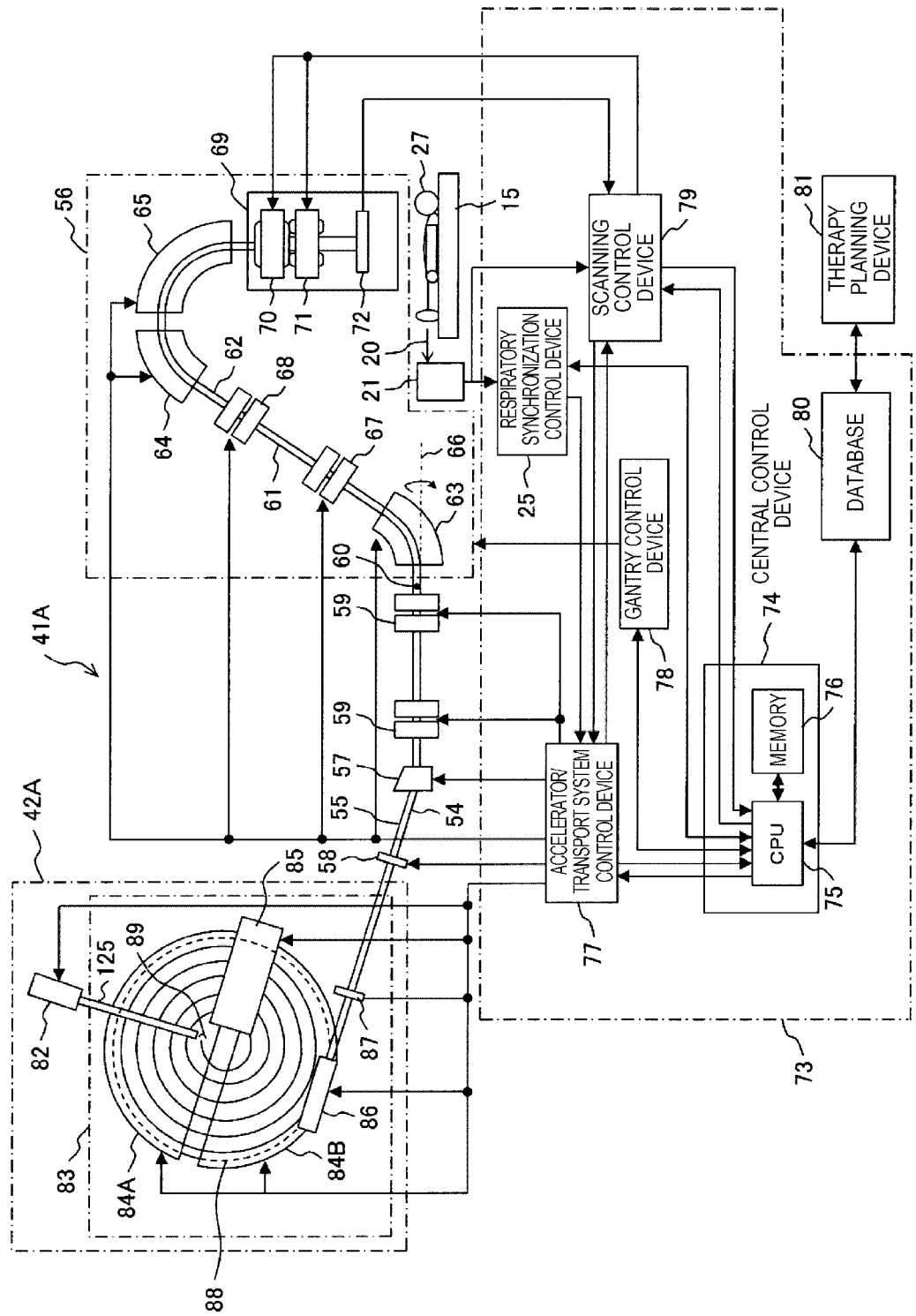
FIG. 17 is a configuration diagram of a particle beam therapy apparatus which is a radiation therapy apparatus of Example 6 which is still another preferable example of the present invention.

A description will be made of a radiation therapy apparatus of Example 6 which is still another preferable example of the present invention with reference to FIG. 17. The radiation therapy apparatus of the present example is a particle beam therapy apparatus.

A particle beam therapy apparatus 41A of the present example includes an ion beam generation device 42A, an HEBT system 54, a GABT system 61, a rotation gantry 56, an irradiation device 69, and a control system 73. The particle beam therapy apparatus 41A has a configuration in which the ion beam generation device 42 is replaced with the ion beam generation device (radiation generation device) 42A in the particle beam therapy apparatus 41 of Example 5. Other configurations of the particle beam therapy apparatus 41A are the same as those of the particle beam therapy apparatus 41. The ion beam generation device 42A has a cyclotron accelerator 83 instead of the synchrotron accelerator 43 unlike the ion beam generation device 42.

In the particle beam therapy apparatus 41A, a configuration of the ion beam generation device 42A will be described focusing on differences from the ion beam generation device 42. The ion beam generation device 42A includes an ion source 82 and the cyclotron accelerator 83 unlike the ion beam generation device 42 used in Example 5. The ion beam generation device 42A is not provided with the linear accelerator 45. The cyclotron accelerator 83 includes a circular vacuum container 88, deflection electromagnets 84A and 84B, a high frequency acceleration device 85, and an emission deflector 86. A vacuum duct 125 connected to the ion source 82 extends to a central position of the vacuum container 88 of the cyclotron accelerator 83, so as to be connected to the vacuum container 88. An incidence electrode 89 curved in a horizontal plane is disposed in the vacuum container 88 in the vicinity of an open end of the vacuum duct 125. The deflection electromagnets 84A and 84B respectively have semicircular shapes, and are disposed such that linear parts thereof face each other, so as to respectively cover an upper surface and a lower surface of the vacuum container 88.

The emission deflector 86 provided at an ion beam emission port of the vacuum container 88 is connected to the beam path 55 of the HEBT system 54. A metallic degrader 87 is attached to the beam path 55 between the emission deflector 86 and the shutter 58. The degrader 87 has a function of adjusting energy of an ion beam emitted from the cyclotron accelerator 83, and has a plurality of metallic plates (not illustrated) of which thicknesses are different from each other. The metallic plates are movable in a direction perpendicular to the beam path 55. The plates having different thicknesses are inserted into the beam path 55 alone or in a plurality so as to cross the beam path 55, and thus an attenuation amount of energy of an ion beam is controlled. As a result, energy of an ion beam applied to an affected part of the patient 27 can be changed, and thus an ion beam can be emitted to the respective layers present in the depth direction of the affected part.

In the particle beam therapy apparatus 41A, the scanning control device 79 of the control system 73 has the same configuration as that of the scanning control device 79 of the particle beam therapy apparatus 41 of Example 5, and the central control device 74 has the substantially same function as that of the central control device 74 of the particle beam therapy apparatus 41. The accelerator/transport system control device 77 of the particle beam therapy apparatus 41A uses the cyclotron accelerator 83, and thus is partially different from the accelerator/transport system control device 77 of the particle beam therapy apparatus 41 in terms of control targets. The accelerator/transport system control device 77 of the particle beam therapy apparatus 41A controls the shutter 58, the deflection electromagnet 57, and the quadrupole electromagnets 59 of the HEBT system 54, and the deflection electromagnets 63 to 65 and the quadrupole electromagnets 67 and 68 of the GABT system 61 in the same manner as the accelerator/transport system control device 77 of the particle beam therapy apparatus 41, and also controls the ion source 82, the deflection electromagnets 84A and 84B, the high frequency acceleration device 85, the emission deflector 86, and the degrader 87.

A description will be made of cancer therapy using the particle beam therapy apparatus 41A. The respective processes in steps S1 to S5, S7 to S9, S9A, S10, S11, and S14 to S17 in the same manner as cancer therapy using the particle beam therapy apparatus 41 of Example 5. In step S2, the ion source 82 is activated, but a linear accelerator is not activated. The radiation detectors 18 are inserted into the body of the patient 27 on the bed 15.

The accelerator/transport system control device 77 performs the respective processes in steps S1 to S3, and S5. In the same manner as in Example 2, in step S1, the shutter 58 is opened by the accelerator/transport system control device 77, and thus the respective electromagnets provided in the HEBT system 54 and the GABT system 61 are excited. In step S2, the ion source 82 is activated, and proton ions generated in the ion source 82 are incident to the center of the vacuum container 88 of the cyclotron accelerator 83 from the incidence electrode 89 through the vacuum duct 125. The deflection electromagnets 84A and 84B are already excited. In step S3, the proton ions which are incident into the vacuum container 88 are accelerated by the high frequency acceleration device 85, and thus a proton ion beam having high energy is generated.

In step S4, the irradiation position control device of the scanning control device 79 adjusts deflection electromagnetic forces of the scanning electromagnets 70 and 71 such that the ion beam reaches the irradiation spot $A_{1,1}$ in the deepest layer $L_1$ of the affected part. Next, the ion beam accelerated by the cyclotron accelerator 83 in step S3 is emitted to the beam path 55 from the emission deflector 86 (step S5), and is applied to the affected part of cancer of the patient 27 on the bed 15 from the irradiation device 69. Thereafter, the respective processes in steps S7 to S9, S9A, S10, and S11 are performed in the same manner as in Example 5. In step S9A, in a case where a beam irradiation stopping signal is output from the dose determination device, the accelerator/transport system control device 77 having received the beam irradiation stopping signal stops the ion source 82, and also inserts the shutter 58 into the beam path 55. Consequently, the irradiation spot $A_{i,j}$ in the layer $L_i$ of the affected part is stopped being irradiated with an ion beam (step S10). In a case where either one of stopping of the ion source 82 and insertion of the shutter 58 is performed, the irradiation spot $A_{i,j}$ is stopped being irradiated with an ion beam. Also in the present example, irradiation with an ion beam on the irradiation spot $A_{i,j}$ is respiration synchronized irradiation performed by the respiratory synchronization control device 25 in the same manner as in the Example.

In a case where a determination result in step S11 is "No", the respective corresponding steps are repeatedly performed until a determination result in step S11 is "Yes" in the same manner as in Example 5, and, in a case where a determination result in step S16 is "No", the respective corresponding steps are repeatedly performed until a determination result in step S16 is "Yes" in the same manner as in Example 5. In a case where a determination result in step S16 is "Yes", therapy of the affected part using irradiation with an ion beam is finished.

In the present example, the respective effects achieved in Example 5 can be achieved.

Example 7

Figure 18:
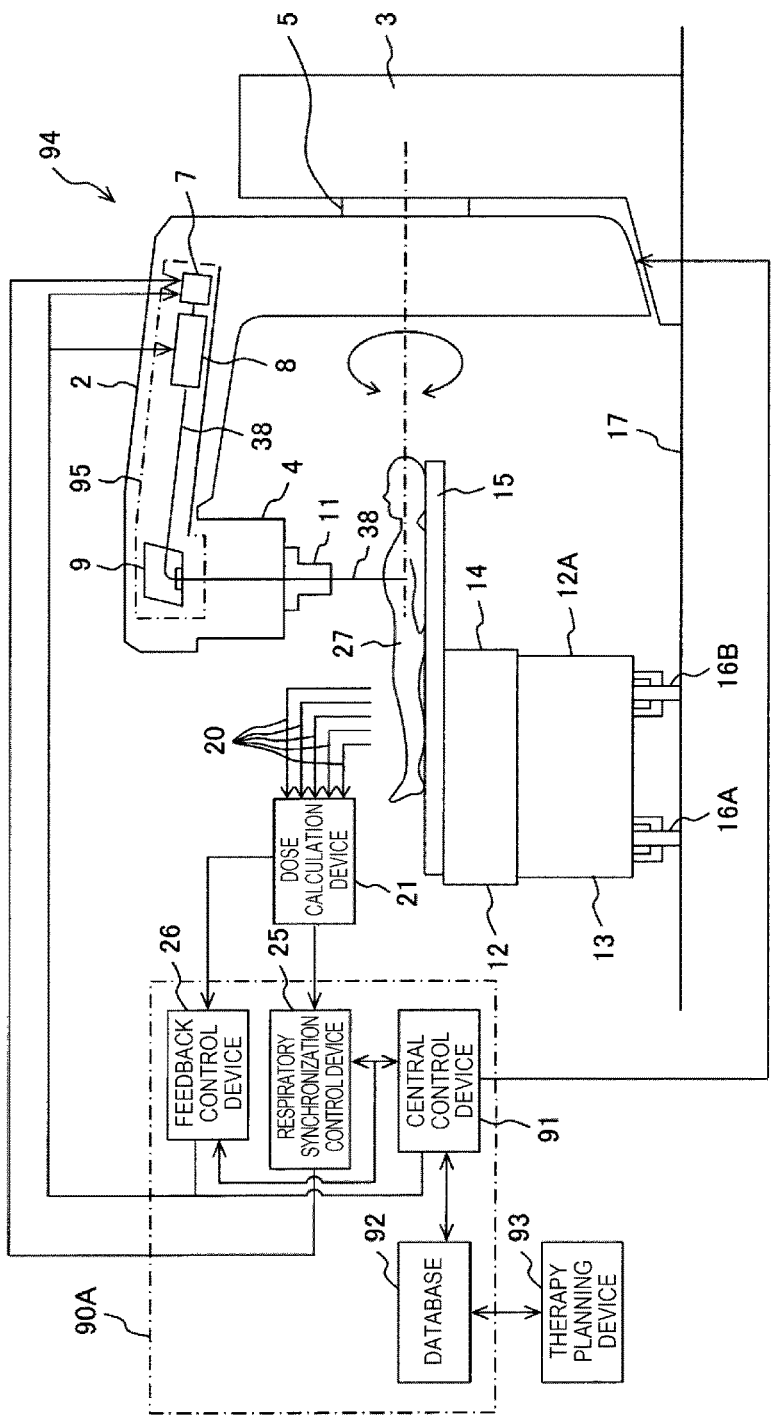
FIG. 18 is a configuration diagram of an electron beam therapy apparatus which is a radiation therapy apparatus of Example 7 which is still another preferable example of the present invention.

A description will be made of a radiation therapy apparatus of Example 7 which is still another preferable example of the present invention with reference to FIG. 18. The radiation therapy apparatus of the present example is an electron beam therapy apparatus.

An electron beam therapy apparatus 94 of the present example has a configuration in which the X-ray generation device 6 is replaced with an electron beam generation device (radiation generation device) 95 in the X-ray therapy apparatus 1A used in Example 2. Other configurations of the electron beam therapy apparatus 94 are the same as those of the X-ray therapy apparatus 1A. The electron beam generation device 95 has a configuration in which the target 10 is removed from the X-ray generation device 6. In other words, the electron beam generation device 95 includes the electron beam generation portion 7, the linear accelerator 8, and the deflection electromagnet 9, and is provided at the arm portion of the rotation gantry 2.

A description will be made of cancer therapy in the present example. In the cancer therapy of the present example, a radiation applied to an affected part, an X-ray is replaced with an electron beam (an aggregate of electrons). Also in the present example, the radiation detectors 18 are inserted into the body of the patient 27 on the bed 15.

In response to a rotation control command from the central control device 91, the rotation gantry 2 is rotated such that the central line of the irradiation head 4 matches an X-ray irradiation direction defined in a therapy plan. An opening shape of the variable collimator 11 is adjusted to a predetermined shape by the central control device 91 controlling the variable collimator. The central control device 91 outputs an activation control command to the electron beam generation portion 7. The electron beam generation portion 7 having received the activation control command generates an electron beam, and the electron beam is accelerated in the linear accelerator 8 so as to become the electron beam 38. The electron beam 38 is bent toward the central line of the irradiation head 4 by the deflection electromagnet 9, and advances along the central line so as to be applied to the affected part of the patient 27 on the bed 15 through the variable collimator 11.

The electron beam applied to the affected part is incident to the light emitting portion 19 of the radiation detector 18 in the body, and a photon is detected. In the same manner as in Example 2, the photons are converted into electric pulses by the photoelectric converter 22, the counting unit 23 counts the electric pulses so as to obtain a counting rate of the electric pulses, and the dose calculation unit 24 converts the counting rate of the electric pulses into a dose rate by using the information of the data table (characteristics in FIG. 6). The dose calculation unit 24 obtains a dose by using the dose rate.

In the present example, in the same manner as in Example 2, the respiratory synchronization control device 25 performs respiration synchronized irradiation with an electron beam by using the information indicating the cyclic change in the dose rate associated with body motion of the patient, illustrated in FIG. 13. Also in the present example, the feedback control device 26 performs feedback control based on the respective processes in steps S3 to S5 in the same manner as in Example 2.

The present example can achieve the respective effects of (1) to (5) achieved in Example 2.

As still another example of an electron beam therapy apparatus which is a radiation therapy apparatus, electron beam therapy apparatuses having a configuration in which the X-ray generation device 6 of the X-ray therapy apparatus 1B (FIG. 14) of Example 3 and the X-ray therapy apparatus 1C (FIG. 15) of Example 4 is replaced with the electron beam generation device (radiation generation device) 95 may be used.

REFERENCE SIGNS LIST 1, 1a, 1b, and 1c: x-ray therapy apparatus
2 and 56: rotation gantry
4: irradiation head
11: variable collimator
6: x-ray generation device
7: electron beam generation portion
8 and 45: linear accelerator
10: target
15: bed
18: radiation detector
19: light emitting portion
20: optical fiber
21: dose calculation device
23: counting unit
24: dose calculation unit
25: respiratory synchronization control device
26: feedback control device
73, 90, 90a, and 90b: control system
74 and 91: central control device
81 and 93: therapy planning device
41 and 41a: particle beam therapy apparatus
42 and 42a: ion beam generation device
43: synchrotron accelerator
48: high frequency acceleration device (high frequency acceleration cavity)
49: high frequency applying device
50: emission high frequency electrode
54 high energy transport system
55 and 62: beam path
61: gantry beam transport system
69: irradiation device
70 and 71: scanning electromagnet
77: accelerator/transport system control device
79: scanning control device
87: degrader
82: ion source
94: electron beam therapy apparatus
95: electron beam generation device

The invention claimed is:

1. A radiation therapy apparatus comprising:
a radiation generation device that generates radiation;
a rotation gantry in which the radiation generation device is provided;
a radiation detector that is insertable into a body of a patient, and has a light emitting portion detecting the radiation and outputting photons;
a calculation device that obtains a counting rate of the photons output from the radiation detector, obtains a dose rate on the basis of the photon counting rate, and obtains a dose on the basis of the dose rate; and
a first control device that performs any one of first control of either controlling the radiation generation device such that the dose obtained by the calculation device becomes a set dose or controlling the radiation generation device such that the dose rate obtained by the calculation device becomes a first set dose rate in feedback control, second control of either adjusting a shape of an opening of a variable collimator attached to an irradiation head provided in the rotation gantry such that the dose becomes the set dose or adjusting the shape of the opening of the variable collimator such that the dose rate becomes the first set dose rate, and third control of either adjusting a position of a bed supporting a radiation irradiation target such that the dose becomes the set dose or adjusting the position of the bed such that the dose rate becomes the first set dose rate.

2. The radiation therapy apparatus according to claim 1, wherein the light emitting portion contains at least one rare earth element.

3. The radiation therapy apparatus according to claim 1, wherein the calculation device includes
a conversion device that converts the photons output from the light emitting portion into electric pulses,
a counting device that obtains a counting rate of the electric pulses output from the conversion device, and
a calculation unit that obtains a dose rate on the basis of the counting rate of the electric pulses, and obtains a dose on the basis of the dose rate.

4. The radiation therapy apparatus according to claim 1, wherein the radiation therapy apparatus is an X-ray therapy apparatus, and
wherein the X-ray therapy apparatus includes an X-ray generation device that is the radiation generation device and generates an X-ray which is the radiation.

5. The radiation therapy apparatus according to claim 1, wherein the radiation therapy apparatus is an X-ray therapy apparatus, wherein the X-ray therapy apparatus includes an X-ray generation device that is the radiation generation device and generates an X-ray which is the radiation, and wherein the first control device controls the X-ray generation device so as to adjust an intensity of the X-ray generated by the X-ray generation device, in the first control.

6. The radiation therapy apparatus according to claim 1, wherein the radiation therapy apparatus is an X-ray therapy apparatus, wherein the X-ray therapy apparatus includes an X-ray generation device that is the radiation generation device and generates an X-ray which is the radiation, and wherein the first control device controls the X-ray generation device so as to adjust energy of the X-ray generated by the X-ray generation device, in the first control.

7. A radiation therapy apparatus comprising:

a radiation generation device that generates radiation;

a radiation detector that is insertable into a body of a patient, and has a light emitting portion detecting the radiation and outputting photons;

a calculation device that obtains a counting rate of the photons output from the radiation detector, and obtains a dose rate on the basis of the photon counting rate; and a second control device that controls the radiation generation device such that a radiation irradiation target is irradiated with the radiation in a case where the dose rate obtained by the calculation device is equal to or lower than a second set dose rate in respiratory synchronization control, and the radiation irradiation target is stopped being irradiated with the radiation in a case where the dose rate exceeds the second set dose rate.

8. The radiation therapy apparatus according to claim 7, wherein the calculation device is a calculation device which obtains a dose rate on the basis of the counting rate of the photons, and obtains a dose on the basis of the dose rate, and wherein the radiation therapy apparatus further comprises a rotation gantry in which the radiation generation device is provided, and a first control device that performs any one of first control of either controlling the radiation generation device such that the dose obtained by the calculation device becomes a set dose or controlling the radiation generation device such that the dose rate obtained by the calculation device becomes a first set dose rate in feedback control, second control of either adjusting a shape of an opening of a variable collimator attached to an irradiation head provided in the rotation gantry such that the dose becomes the set dose or adjusting the shape of the opening of the variable collimator such that the dose rate becomes the first set dose rate, and third control of either adjusting a position of a bed supporting a radiation irradiation target such that the dose becomes the set dose or adjusting the position of the bed such that the dose rate becomes the first set dose rate.

9. The radiation therapy apparatus according to claim 7, wherein the radiation therapy apparatus is a particle beam therapy apparatus, and wherein the particle beam therapy apparatus includes an ion beam generation device that is the radiation generation device and generates a particle beam which is the radiation, a beam transport system that guides the beam emitted from the ion beam generation device, a rotation gantry, and an irradiation device that is provided in the rotation gantry, and applies the beam which is input from the beam transport system to the radiation irradiation target.

10. The radiation therapy apparatus according to claim 9, wherein the light emitting portion contains at least one rare earth element.

11. The radiation therapy apparatus according to claim 9, wherein the calculation device includes a conversion device that converts the photons output from the light emitting portion into electric pulses, a counting device that obtains a counting rate of the electric pulses output from the conversion device, and a calculation unit that obtains a dose rate on the basis of the counting rate of the electric pulses, and obtains a dose on the basis of the dose rate.

12. The radiation therapy apparatus according to claim 7, wherein the radiation therapy apparatus is an electron beam therapy apparatus, and wherein the electron beam therapy apparatus includes an ion beam generation device that is the radiation generation device and generates an electron beam which is the radiation.

* * * * *